(12) United States Patent
Willis et al.

(10) Patent No.: US 7,008,449 B2
(45) Date of Patent: Mar. 7, 2006

(54) REFRACTIVE INTRAOCULAR IMPLANT LENS AND METHOD

(76) Inventors: Timothy R. Willis, 1004 Denfield Ct. Suite 250, Raleigh, NC (US) 27609; Lyle E. Paul, 451 Bluebird Dr., Russell, KY (US) 41169; Joseph Collin, 59 Rue de Parc, Bordeaux (FR)

( * ) Notice: Subject to any disclaimer, the term of this patent is extended or adjusted under 35 U.S.C. 154(b) by 0 days.

(21) Appl. No.: 10/919,171

(22) Filed: Aug. 16, 2004

(65) Prior Publication Data

US 2005/0015143 A1    Jan. 20, 2005

Related U.S. Application Data

(63) Continuation-in-part of application No. 09/774,127, filed on Jan. 30, 2001, now Pat. No. 6,827,738.

(51) Int. Cl.
*A61F 2/16* (2006.01)

(52) U.S. Cl. ..................... 623/6.36; 623/6.52
(58) Field of Classification Search ....... 623/6.38–6.55
See application file for complete search history.

(56) References Cited

U.S. PATENT DOCUMENTS

| | | | |
|---|---|---|---|
| 4,053,953 A | 10/1977 | Flom | |
| 4,126,904 A | 11/1978 | Shepard | |
| 4,166,293 A | 9/1979 | Anis | |
| 4,177,526 A | 12/1979 | Kuppinger | |
| 4,215,440 A | 8/1980 | Worst | |
| 4,343,050 A | 8/1982 | Kelman | |
| 4,535,488 A | 8/1985 | Haddad | |
| 4,536,895 A | 8/1985 | Bittner | |
| 4,575,374 A | 3/1986 | Anis | |
| 4,589,147 A * | 5/1986 | Nevyas | ............ 623/6.54 |
| 4,676,794 A * | 6/1987 | Kelman | ............ 623/6.54 |
| 4,863,462 A | 9/1989 | Fedorov | |
| 5,047,052 A | 9/1991 | Dubroff | |
| 5,192,319 A | 3/1993 | Worst | |
| 5,628,796 A | 5/1997 | Suzuki | |
| 5,928,282 A | 7/1999 | Nigam | |
| 6,051,024 A | 4/2000 | Cumming | |
| 6,699,284 B1 * | 3/2004 | Sunada | ............ 623/6.54 |
| 6,827,738 B1 * | 12/2004 | Willis et al. | ............ 623/6.43 |

FOREIGN PATENT DOCUMENTS

WO    WO/92/20302    11/1992

OTHER PUBLICATIONS

"Ocular Surgery News", Sep. 1, 2000 5 Pages.

* cited by examiner

*Primary Examiner*—David H. Willse
*Assistant Examiner*—Hieu Phan
(74) *Attorney, Agent, or Firm*—Robert G. Rosenthal

(57) ABSTRACT

A refractive intraocular lens (104) and method of locating the lens within the eye and attaching the lens to the iris. The refractive intraocular lens (104) may be attached via a staple (230), a fastener (312), anchor (412) or by the tip of the haptic (118).

10 Claims, 23 Drawing Sheets

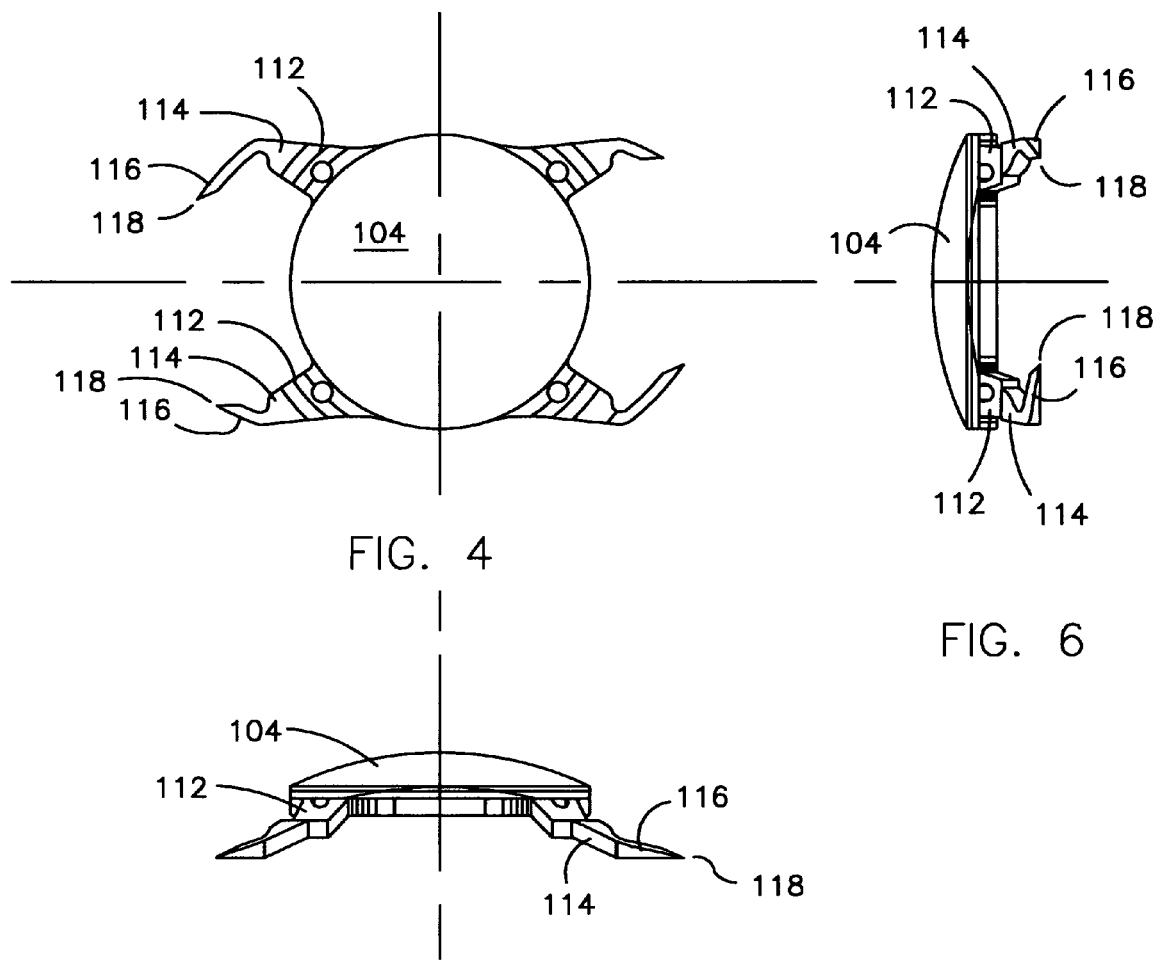

SECTION A-A

SECTION A — A

SECTION A — A

SECTION A – A

SECTION A – A

REFRACTIVE INTRAOCULAR IMPLANT LENS AND METHOD

PRIORITY CLAIM

This application is a continuation-in-part of U.S. patent application Ser. No. 09/774,127 filed Jan. 30, 2001 now U.S. Pat. No. 6,827,738.

FIELD OF THE INVENTION

This invention relates generally to the field of intraocular implant lenses and more particularly, to intraocular implant lenses for use in refractive vision correction.

BACKGROUND OF THE INVENTION

It has long been a goal of ophthalmic surgeons to provide patients with alternatives to eyeglasses. Witness the development of the contact lens, radial keratotomy and lasik or laser vision correction surgery. It is estimated that in the year 2000, over two million Lasik procedures will be performed. Notwithstanding the popularity of laser surgery, it is not without its drawbacks and deficiencies. For example, recent data has shown that approximately 5–10% of the patients undergoing laser refractive surgery will have suboptimal results such as, a final vision correction which still requires some sort of optical correction or the patient will experience cataract-like "halos". In addition, it has been estimated that up to 50% of the patients post laser surgery experience dry eye symptoms on an ongoing basis.

In response to the foregoing, ophthalmic surgeons have turned to intraocular implant surgery in an effort to advance the art of refractive vision correction. For example, U.S. Pat. No. 5,192,319 to Worst discloses an intraocular refractive lens which is surgically positioned in the anterior chamber and is used in addition to the natural lens to correct for myopic and hyperopic refraction error. The lens comprises an optical portion (the optic) having an inner concave and an outer convex shape. Attached to the outer periphery of the optic is one or more pairs of flexible pincer arms which are adapted to pinch a small portion of the anterior surface of the iris to maintain the implant in place. Notwithstanding the foregoing, the Worst lens has not been widely adopted. This is because the lens requires a hard, non-flexible material to fixate to the iris, thus requiring a large 6 mm or more incision. Also, the amount of tissue contact of greater than 7 square mm with the implant and the iris have caused clinical issues of endothelial cell loss of greater than two per cent (2%) per year, whereas normal cell loss is one per cent (1%) per year. In addition, the Worst lens is difficult to implant and requires a two handed ambidextrous surgical technique to insert and attach to the iris, skills, which are found in relatively few ophthalmologists.

Other anterior chamber implants have also been attempted without success. For example, U.S. Pat. No. 4,575,374 to Anis discloses an anterior chamber lens comprising an optic and four haptics, each of which flexes independently of the others. U.S. Pat. No. 4,166,293 also to Anis discloses an anterior chamber implant for cataract replacement having an optic and three loops that extend downward and are adapted to fit behind the iris. A fourth loop overlies on of the other loops and overlies the iris when the implant is in place within the eye. The implant is held in place by an attachment member, which connects the fourth loop with the underlying loop by penetrating through the iris. Another anterior chamber implantable lens is disclosed in U.S. Pat. No. 4,177,526 to Kuppinger wherein a pair of opposing arms are attached to the optic. The respective arms are inserted behind the iris and pinch the rear of the iris to hold the implant in place. Another anterior chamber implant lens is disclosed in U.S. Pat. No. 5,047,052 to Dubroff, which teaches an optic, and four haptics extend outwardly therefrom. The haptics are flexible and independently movable. Further, once the implant is inserted and positioned by conventional means, the ends of the haptics are adapted to rest within the optical angle, i.e., the intersection of the cornea and the iris. It is notable that none of the foregoing implant lenses have been widely adopted and in fact only one of the lens (i.e., Worst Lens) is currently in limited use in the European market, as they all experienced surgical or clinical failures including, lens insertion and attachment problems, intraocular or iris bleeding, inflammation, endothelial cell loss, tissue deformation, or lens induced glaucoma.

Accordingly, it is an object of the present invention to provide an improved refractive implant, which solves the aforementioned problems.

A further object of the present invention is to provide an improved refractive implant, which is minimally surgically invasive and maintains the natural anatomical processes (e.g., fluid flow, endothelial cell loss, etc.) of the eye.

Another object of the present invention is to provide an improved refractive implant having reduced side effects, for example dry eyes and inflammation.

An additional object of the present invention is to provide an improved refractive implant, which is easily implantable and removable, if necessary.

A still further object of the present invention is to provide an improved refractive implant, which accurately corrects vision, thus obviating the need for subsequent surgeries.

A correlated object of the present invention is to provide an improved refractive implant, which is easy to manufacture.

Yet another object of the present invention is to provide an improved refractive implant, which does not require expensive equipment, such as lasers.

SUMMARY OF THE INVENTION

In accordance with the present invention, there is provided a refractive intraocular lens that is adapted to be implanted within the eye and which is supported by the iris. The lens is characterized by its ability to be easily inserted and removed with minimal trauma to the eye tissues. The lens comprises an optic for producing a preselected optical effect having an anterior side, a posterior side and an outer peripheral edge. The lens may be foldable or deformable. A haptic is connected to the optic and extends outwardly therefrom. The haptic includes a proximal end, a distal end and an intermediate segment positioned therebetween. The proximal end is connected to the optic and the intermediate segment projects downwardly and away from the posterior side of the optic and the distal end terminates in a pointed tip. The intermediate segment includes a shoulder for supporting the lens on the iris. The distal end of the haptic includes an iris fixation means for attaching the lens to the iris wherein the tip is constructed and arranged to penetrate the iris.

In a second embodiment of the invention, the refractive intraocular lens is attached to the iris by means of a staple, which is adapted to overlie and straddle a portion of the haptic. The staple is compressible from a first relaxed state to a second expanded state such that when the staple is expanded and placed in an overlying straddling relation to the haptic and is released, the staple contracts and attaches the iris, thereby fixing the position of the intraocular lens thereon. Additionally, the staple could be attached to the iris in the reverse manner from that which is described above.

In a third embodiment of the invention, at least one of the haptics includes a hole defining an opening. A fastener is adapted to be received within the opening and to expandingly grip the iris tissue. More specifically, the fastener comprises a shaft having a top end and a bottom end. The bottom end includes includes a flexible barb and the top has a diameter that is greater than the diameter of the opening such that when the fastener is inserted in the opening, the barb is retracted and the fastener slides in the opening and when the barb exits the bottom of the opening, the iris is hooked and the barb becomes embedded therein, thus attaching the intraocular lens to the iris.

BRIEF DESCRIPTION OF THE DRAWINGS

Some of the objects of the invention having been stated, other objects will appear as the description proceeds when taken in connection with the following detailed description and appended claims, and upon reference to the accompanying drawings.

FIG. 4 is a plan view of an implant lens according to the present invention.

FIG. 5 is an end view of an implant lens according to the present invention.

FIG. 6 is an end view of an implant lens according to the present invention.

DETAILED DESCRIPTION OF THE PREFERRED EMBODIMENTS

While the present invention will be described more fully hereinafter with reference to the accompanying drawings, in which particular embodiments are shown, it is to be understood at the outset that persons skilled in the art may modify the invention herein described while still achieving the favorable results of this invention. Accordingly, the description which follows is to be understood as a broad teaching disclosure directed to persons of skill in the appropriate arts and not as limiting upon the present invention.

Figure 1A:
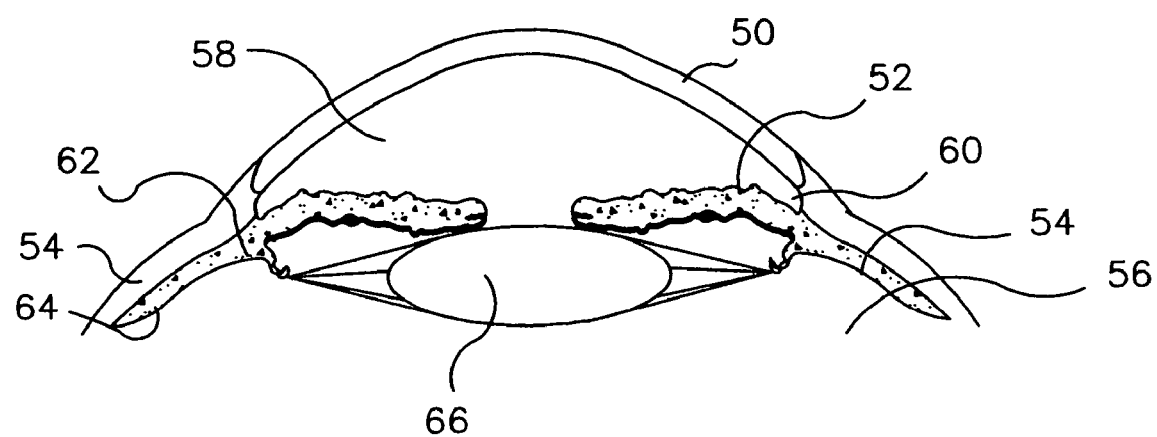
FIG. 1a is a cross section of a human eye.
Figure 1B:
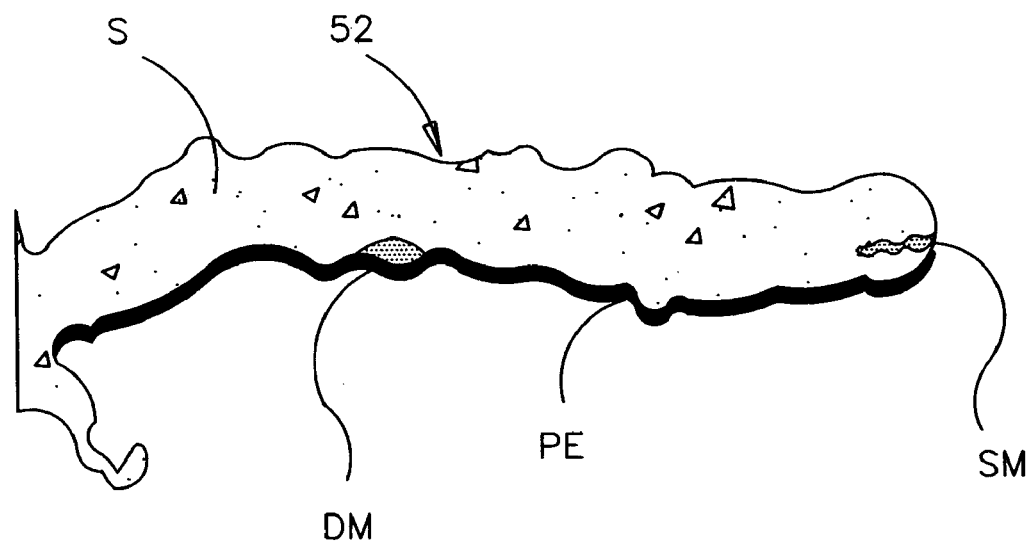
FIG. 1b is a sectional view of one-half of the iris and illustrating the essential structures thereof.
Figure 2:
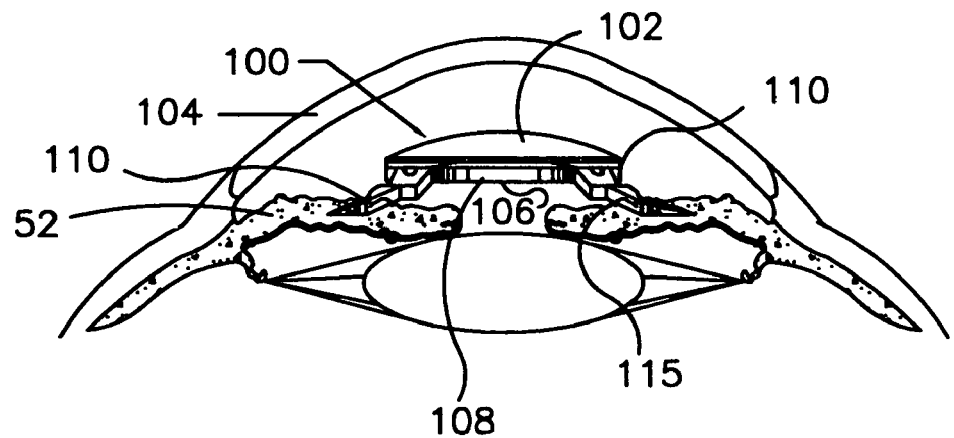
FIG. 2 is a cross section of a human eye with an implant according to the present invention affixed to the iris.
Figure 3:
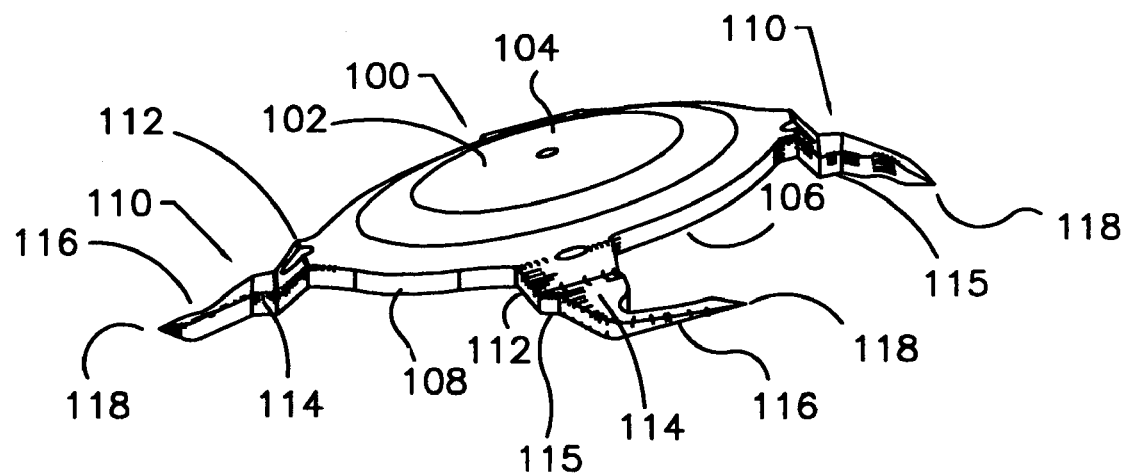
FIG. 3 is a perspective view of an implant lens according to the present invention.

Referring now to the drawings and particularly to FIGS. 1a and 1b in which a human eye is schematically illustrated. The structures of the eye include the cornea 50, iris 52, sclera 54, vitreous 56, anterior chamber 58, chamber angle 60, trabecular meshwork 62, posterior chamber 64 and human crystalline lens 66. The iris 52 controls the amount of light entering the eye and is comprised of the stroma S, a dilator muscle DM and a sphincter muscle SM which are tied together beneath the iris by the pigment epithelium PE. The dilator muscle DM and the sphincter muscle SM are connected together via nerves which run through the pigment epithelium PE and which as a group, operate to control the diameter of the iris opening. Further, the pigment epithelium constitutes approximately five percent (5%) of the total thickness of the iris. While the description which follows includes numerous examples of intraocular lenses, haptics and fasteners which are exemplary of the present invention, it will be noted that the point of contact of the haptic and/or the fastener to the iris must not interfere with the normal operation of the iris. More specifically, the opening and closing of the iris is controlled by the sphincter muscle and the dilator muscle which are functionally interconnected beneath the iris by the pigment epithelium and nerves and nerve endings which are present therein. It will also be noted that nourishment is transferred to the iris from the iris root through throughout the iris.

While the diameter of the iris will vary with the size of the eye as between individuals, the inventors have determined that the distance from the edge of the pupil opening to the leading edge of the dilator muscle is similar in size for all mature human eyes. Further, the inventors have determined that the fact that the dilator muscle and sphincter muscle are not directly connected together and the iris tissue between the muscles does not move provides an ideal location to attach the refractive implant inside the eye while not disturbing the natural working of the eye. In view of the foregoing, so long as the attachment means employed locates between the sphincter and dilator muscles and does not penetrate through and into the pigment epithelium of the iris, the eye will experience minimal trauma over both the short and longer terms and the implant should be well tolerated. Thus, penetration of between 5% and 95% of the iris should securely attach the implant to the iris while not disturbing the nerves in the bottom 5% where the pigment epithelium is located.

In addition, the refractive intraocular lens optical characteristics work with the human optical system, i.e., cornea and human crystalline lens to correct for refractive errors such as myopia, hyperopia, presbyopia and astigmatism. The refractive intraocular lens of the present invention is characterized by its minimal tissue contact area of less than 7 square mm of contact with the iris and preferably between 1.5 and 5.0 square mm and ability to be easily inserted and removed with minimal trauma to the eye tissues.

While the description makes specific reference to the human eye, it will be understood that the invention may be applied to various animals. For example, mammals such as dogs, cats and horses and the like may suffer injuries when their eyesight deteriorates with age and vision correction surgery as contemplated by this invention may prevent injury and thus extend their useful life.

Turning now to FIGS. 2 through 8, a first embodiment of the invention is there illustrated. The intraocular lens generally indicated at 100 is adapted to be implanted within the eye and includes an optical means or optic 102 and a single or a plurality of haptic means or haptics 110. The optic 102 is selected in order to produce the preselected optical effect, e.g., myopia of −1 diopter to −25 diopter, hyperopia of +1 diopter to +10 diopter, astigmatism of +/−1 diopter to +−8 diopter at up to +−180 degrees and presbyopia of 0.5 diopter to 1.5 diopter. The optic may be implanted to supplement the natural (or implanted) lens. The optic is generally circular and has an anterior side 104, a posterior side 106 and an outer peripheral edge 108. The diameter of the optic 102 is in the range of approximately 5 mm to 6 mm. In addition, the optic 102 will have varying anterior and posterior curvatures, depending on whether myopia or hyperopia is being corrected. Further curvature variations are added for the correction of cylinder (Astigmatism), presbyopia, bi-focal or multi-focal. The characteristics of the particular optic 102 selected are left to the surgical judgment of the ophthalmologist performing the implant procedure. In addition, the optic 102 and the haptics 110 must be made of a material, which is biologically inert and the optic 102 must additionally be made of a material, which satisfies the necessary optical and surgical insertion requirements. The term "biologically inert" is generally understood in the art to be a material which is not absorbed by the body fluids and which does not cause any adverse reaction when implanted. Commonly used materials alone or in combination for intraocular lenses are silicone, acrylic, collagen, hydrogel and polymethylmethacrylate. Other suitable materials may include ophthalmic glass, quartz and other polymeric materials.

Figure 7:
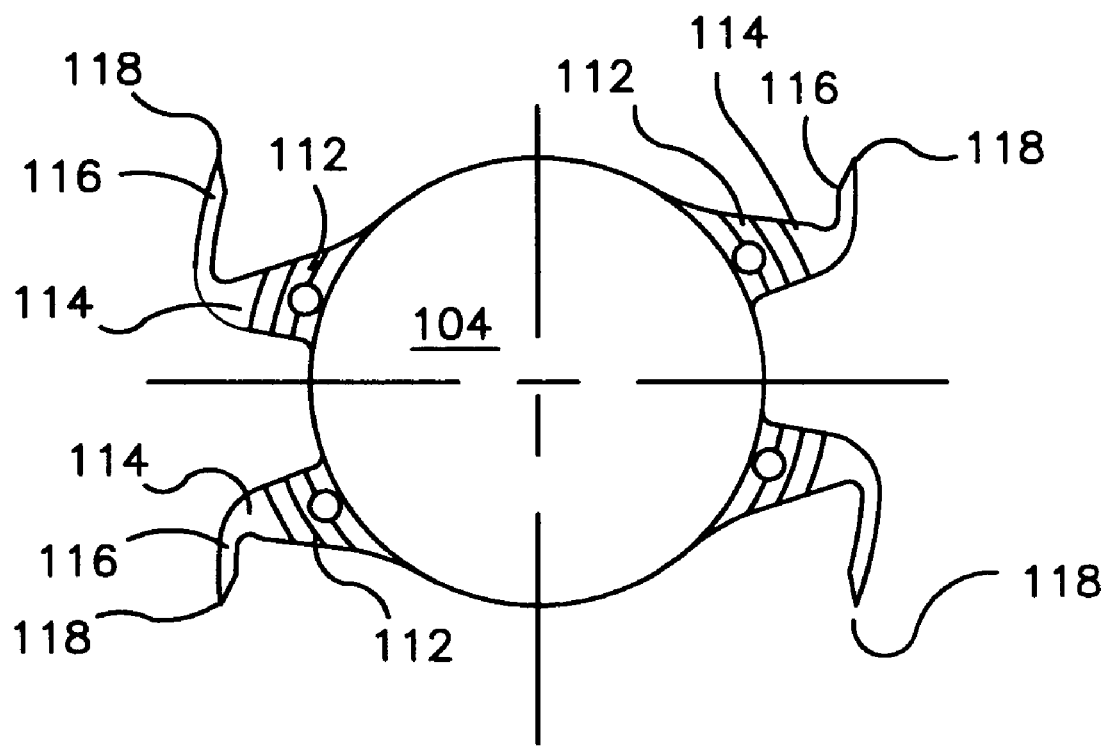
FIG. 7 is a plan view of an implant lens according to the present invention and having a second arrangement of tips.
Figure 8:
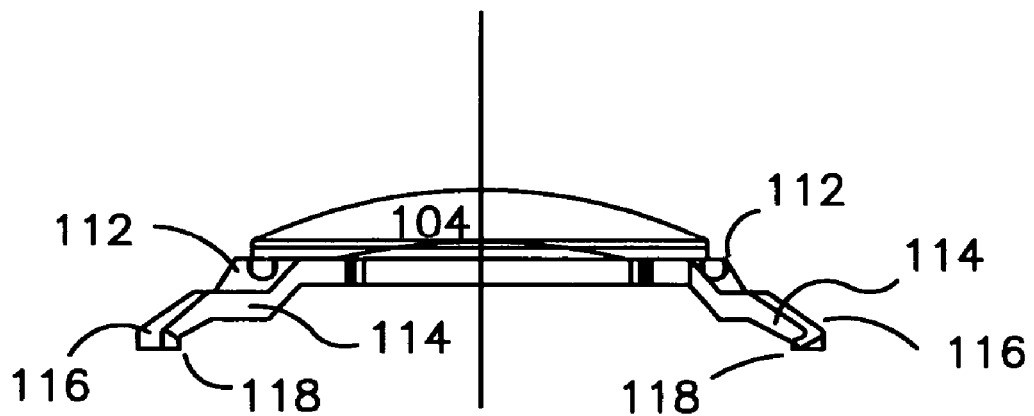
FIG. 8 is an end view of an implant lens according to the present invention and having a second arrangement of tips.
Figure 9:
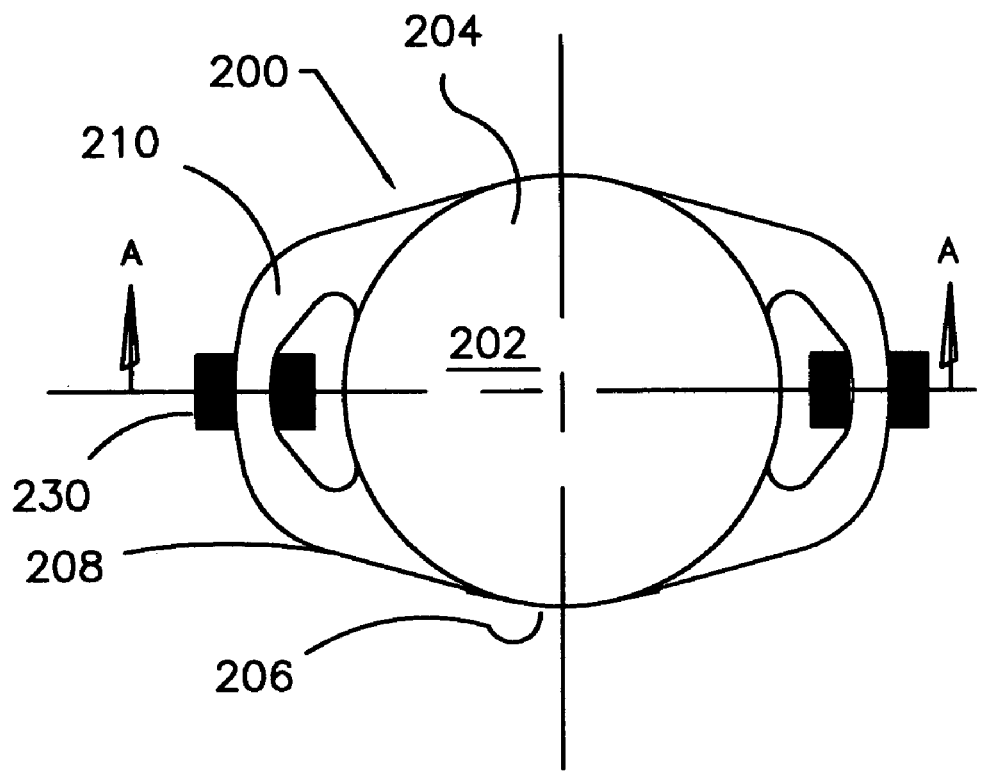
FIG. 9 is a plan view of a second embodiment of the implant lens according to the present invention.

A single or a plurality of haptics 110 are connected to the optic 100. The haptics extend outward from the optic and are spaced apart from each other. Each of haptics 110 include a proximal end 112 which is connected to the outer peripheral edge 108 of the optic, an intermediate segment 114, and a distal end 116. The haptics also include a riser means or riser for maintaining the optic in spaced relation from the iris. In the illustrated embodiment, the intermediate segment 114 includes the riser and it projects downwardly and away from the posterior side of the optic 102 in order to "vault" or provide spacing between the underside of the implant and the surface of the iris. In addition, the intermediate segment 114 includes a shoulder 115 which is adapted to support the implant 100 on the surface of the iris 52. The distal end 116 has at it's terminating end, an iris fixation means or iris connector for attaching the intraocular lens to the iris in the form of a pointed tip 118 which is adapted to penetrate the iris. In the preferred embodiment, penetration is a portion of, but less than the entire iris, and in the preferred embodiment is approximately one half the thickness of the iris. The amount of penetration and contact area will vary with the mass of the implant, the number and structure of haptics, optic to haptic vaulting and other factors. It will be noted that the haptics are of sufficient length so as to avoid interfering with proper "iris function", i.e., the muscles which control the opening and closing of the pupil. Alternatively, the staple may be designed such that it pinches, but does not necessarily penetrate the iris, thereby attaching the intraocular lens. With respect to the embodiment illustrated in FIGS 2 through 6, four haptics are shown. They are divided into two pairs, each of which extends outwardly and away from the optic at opposite ends thereof. In addition, the respective pointed tips 118 of each pair face inwardly towards each other. The embodiment as shown in FIGS 7–8 is essentially identical as that just discussed, however the respective pointed tips 118 are in opposing relation or facing outwardly. Either arrangement will adequately anchor the implant 100 on the iris. Notwithstanding the foregoing, the refractive intraocular lens according to the present invention is characterized by its minimal tissue contact area which is less than about 7.00 square mm and preferably between about 1.5 square mm and 5.00 square mm.

In operation, an incision on the order of 4.0 mm is made in the cornea or sclera by the ophthalmic surgeon. Using forceps or intraocular lens insertion instruments, the implant 100 may be folded, deformed or rolled to reduce the overall insertion size, inserted into the eye and centered over the pupillary opening. Each of the haptics is then manipulated such that the tips penetrate the iris. It will be noted that the respective intermediate segments 114 of the haptics 110 include a shoulder portion, which rests on the iris and limits the depth to which the tips 118 can penetrate.

Figure 11:
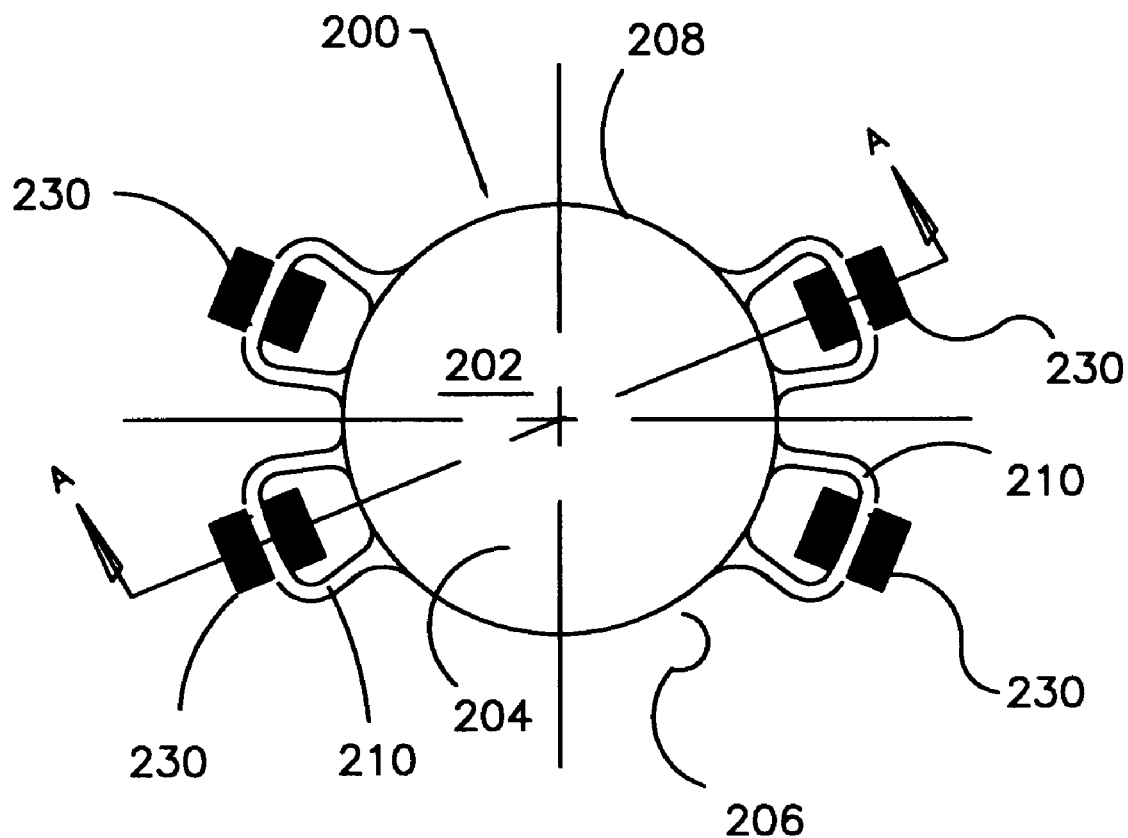
FIG. 11 is a plan view of the second embodiment of the implant lens according to the present invention and having a different haptic arrangement.
Figure 12:
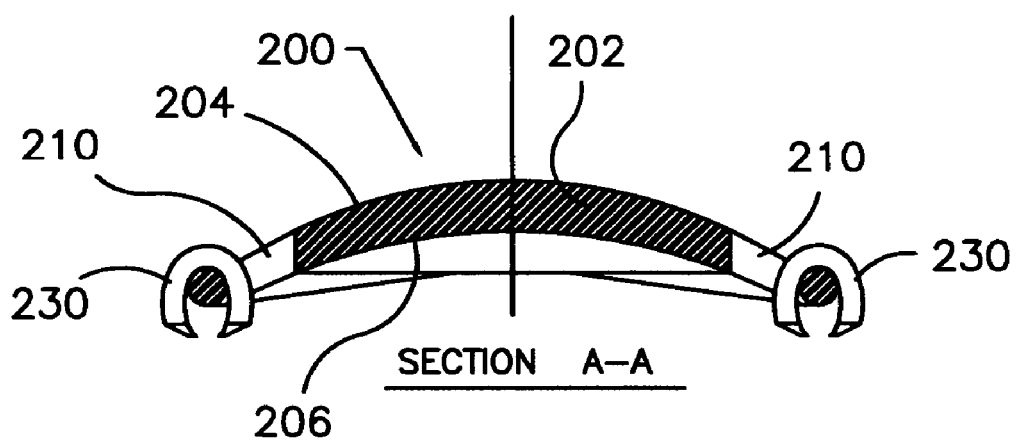
FIG. 12 is a sectional view taken along line A—A of the embodiment of the implant lens of FIG. 11.
Figure 13:
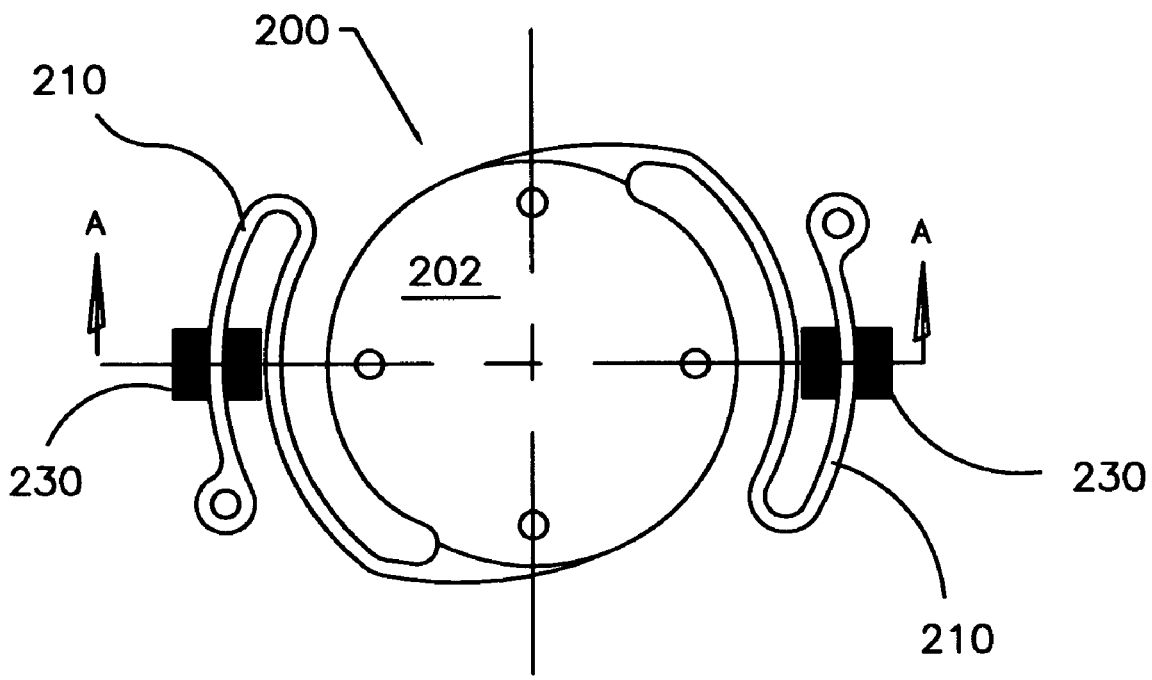
FIG. 13 is a plan view of the second embodiment of the implant lens according to the present invention and having a third haptic arrangement.
Figure 14:
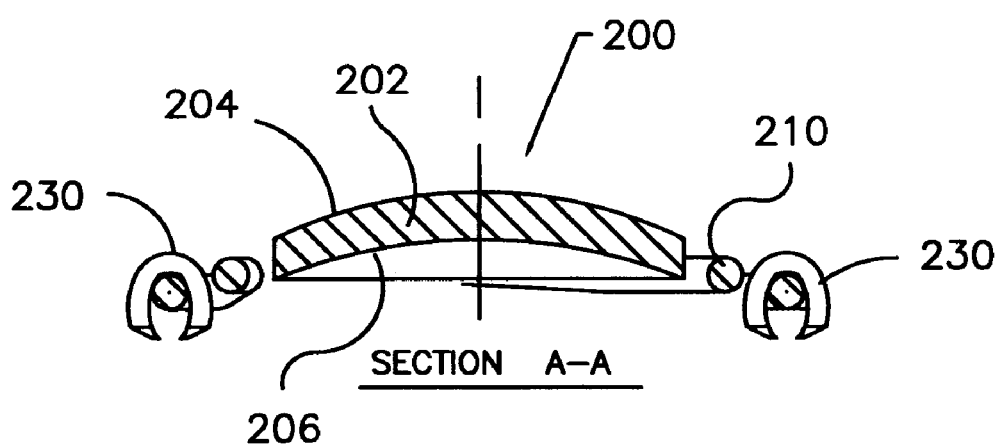
FIG. 14 is a sectional view taken along line A—A of the embodiment of the implant lens of FIG. 13.

A second embodiment of the invention is illustrated in FIGS 9 through 14 wherein an optical implant 200 is adapted to be implanted within the eye and to be attached to the iris. The implant comprises an optical means or optic 202 for producing a preselected optical effect. The optic 202 has an anterior side 204, a posterior side 206 and an outer peripheral edge 208. A single or plurality of haptic means or haptics 210 are connected to the optic 202. A staple means or fastener such as a staple 230 is adapted to straddle a portion of said haptic 210. The staple 230 is adapted to be manipulated from a relaxed state to a tensioned state whereupon it is released and attaches to the iris. In the illustrated embodiment, the staple in the relaxed state is expanded. It is then compressed (with an insertion tool discussed herein below), placed in overlying straddling relation to the respective haptic(s), and upon release, expands to substantially return to its original state, thereby fixing the position of the optical implant thereon. It will be noted that the tensioned and relaxed states could be reversed with equal efficacy. As with the embodiment shown in FIGS 9–14, the staple is dimensioned such that it penetrates a portion of, but less than the entire iris, preferably, approximately one-half the thickness of the iris. The reader will appreciate that the dimensions and degree of iris penetration will vary with the particular type of optical implant used. For example, in FIGS 9 and 10, optical implants having a pair of vaulted loop-type haptics located on opposite sides of the optic is shown with staples. In FIGS 11–12 an optical implant having four vaulted loop-type haptics is shown with staples. Further, the haptics are configured such that the optic is in spaced relation from the iris. In FIGS 13–14 an optical implant with flexible curved haptics is shown with staples 230. In this embodiment, the staple(s) could be located such that the intraocular lens expands and contracts with the dilation of the iris sphincter muscle.

Figure 19:
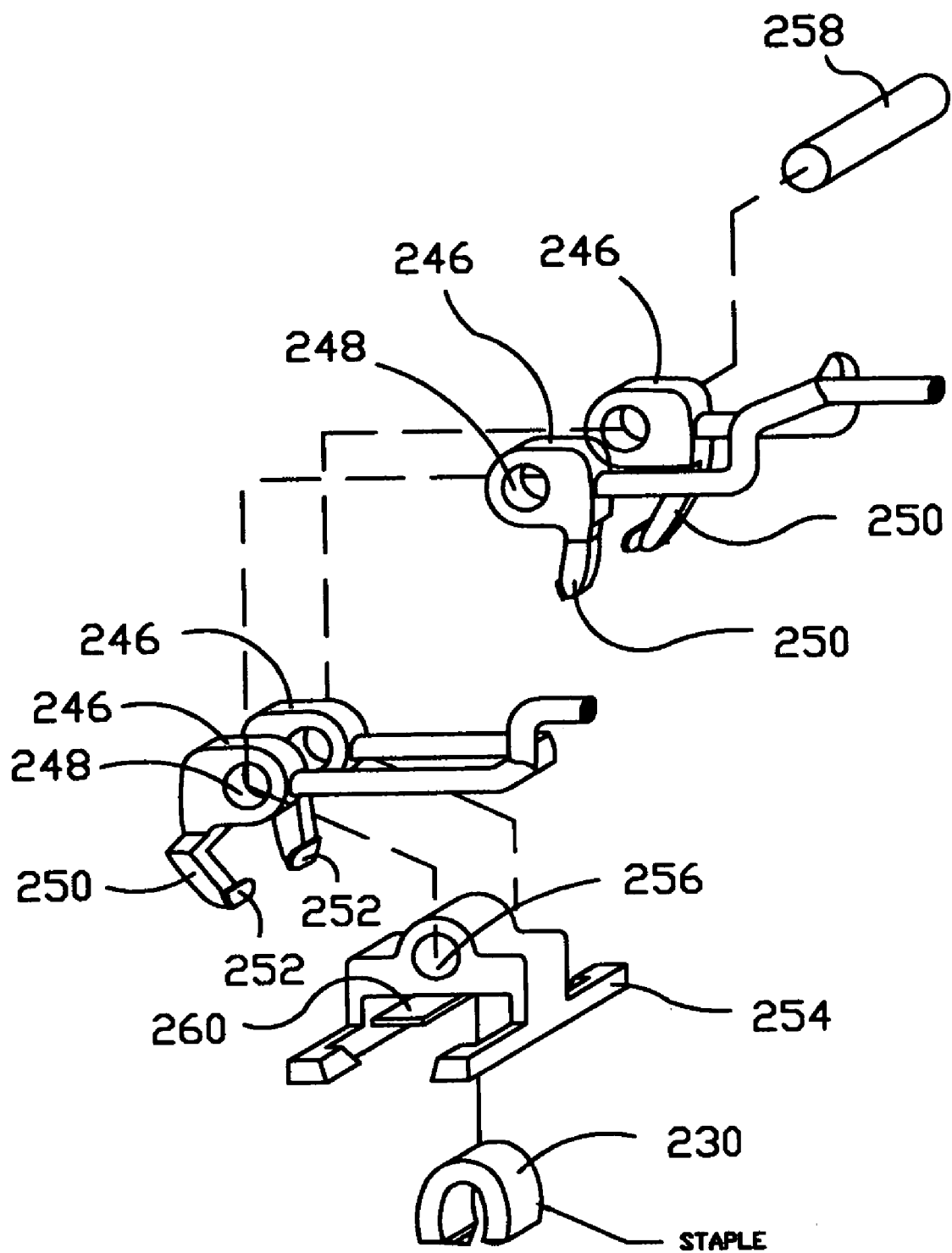
FIG. 19 is an exploded view of the staple insertion tool according to the present invention.
Figure 20:
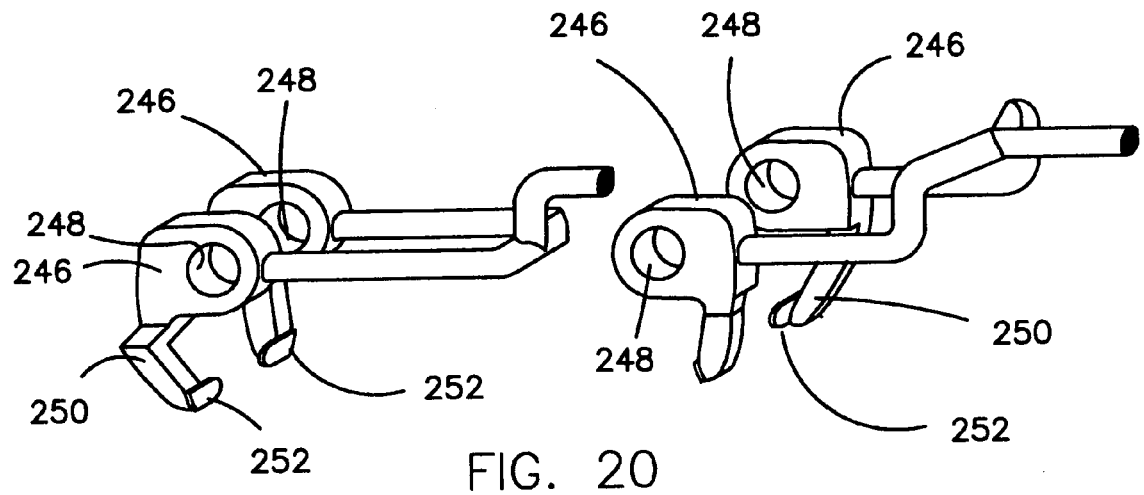
FIG. 20 is a perspective view of a portion of the staple insertion tool according to the present invention.
Figure 21:
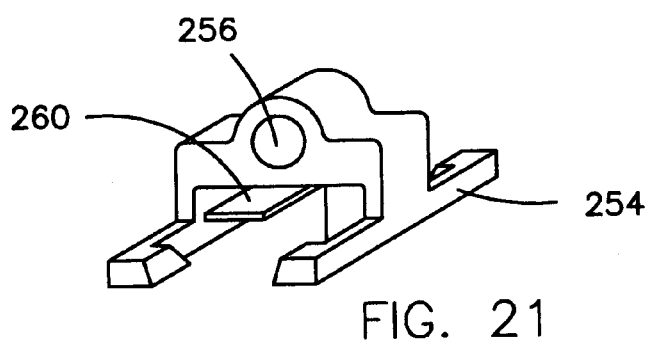
FIG. 21 is a perspective view of the trap lock and gripping fingers portion of the staple insertion tool according to the present invention.
Figure 22:
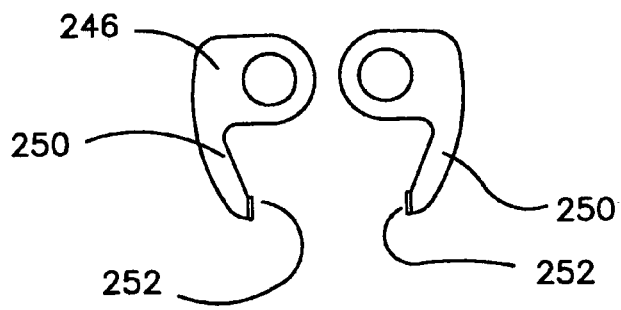
FIG. 22 is a side view of the gripping fingers portion of the staple insertion tool in the open staple releasing position.
Figure 23:
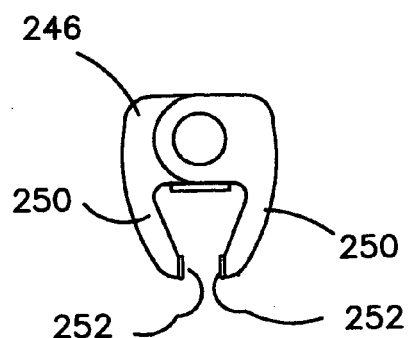
FIG. 23 is a side view of the gripping fingers portion of the staple insertion tool in the closed staple gripping position.
Figure 24:
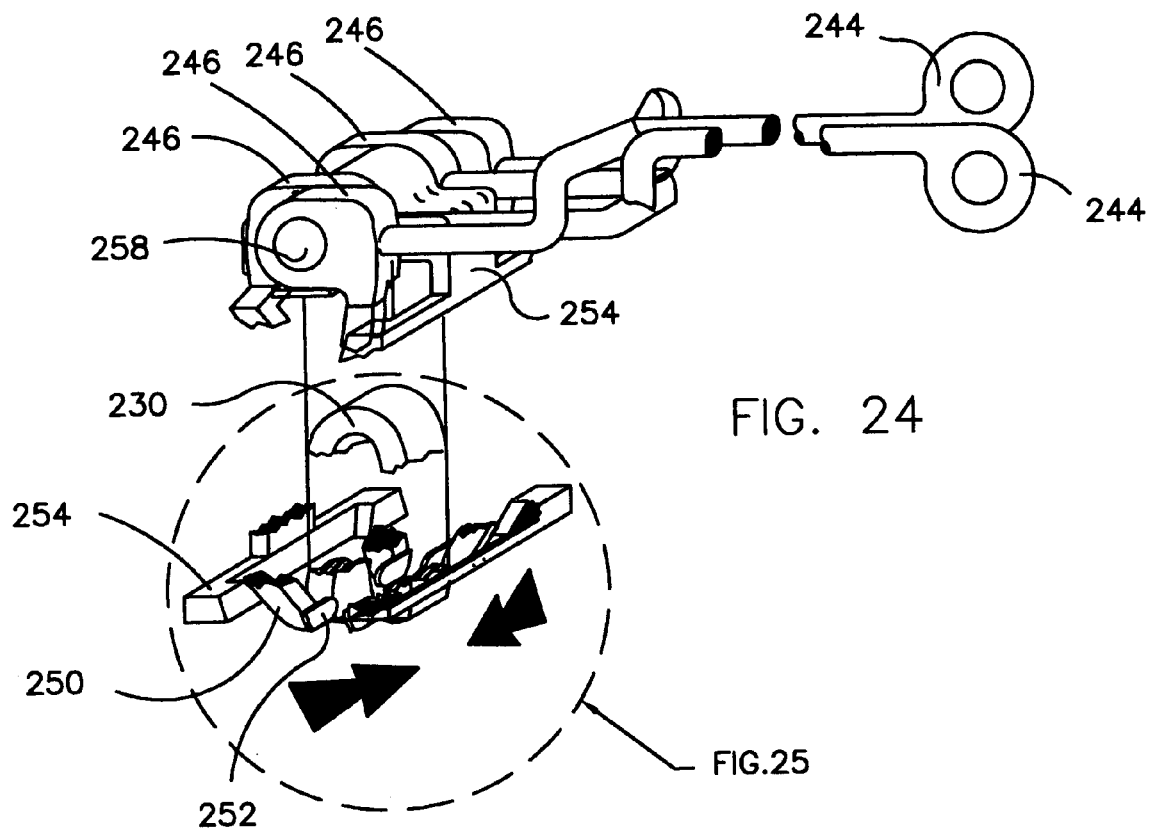
FIG. 24 is a perspective view of the staple insertion tool according to the present invention in the closed staple gripping mode.
Figure 25:
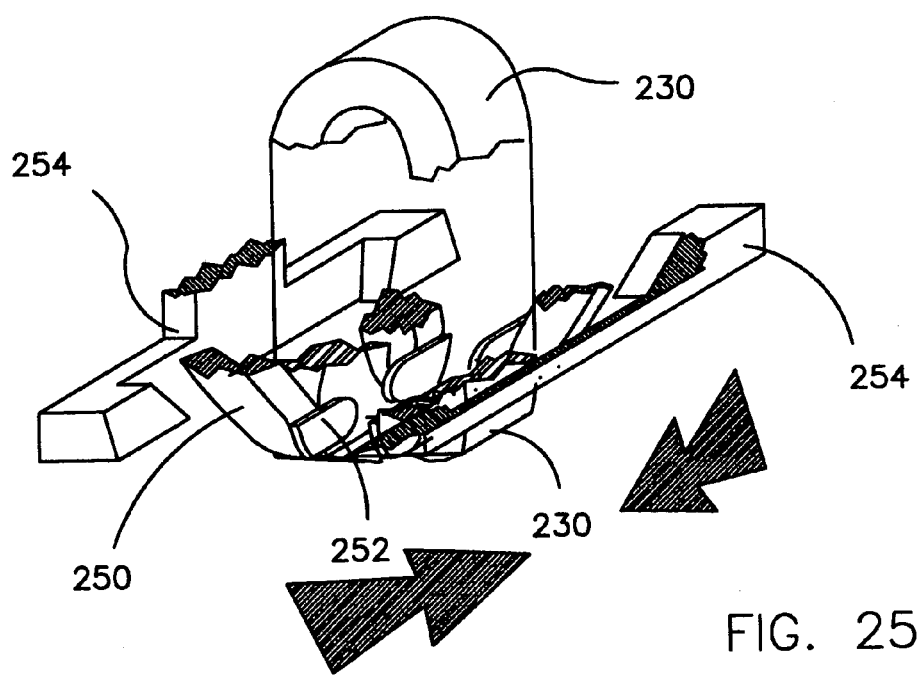
FIG. 25 is a detailed perspective view, partially broken away, of the gripping portion of the tool as illustrated in FIG. 24.
Figure 26:
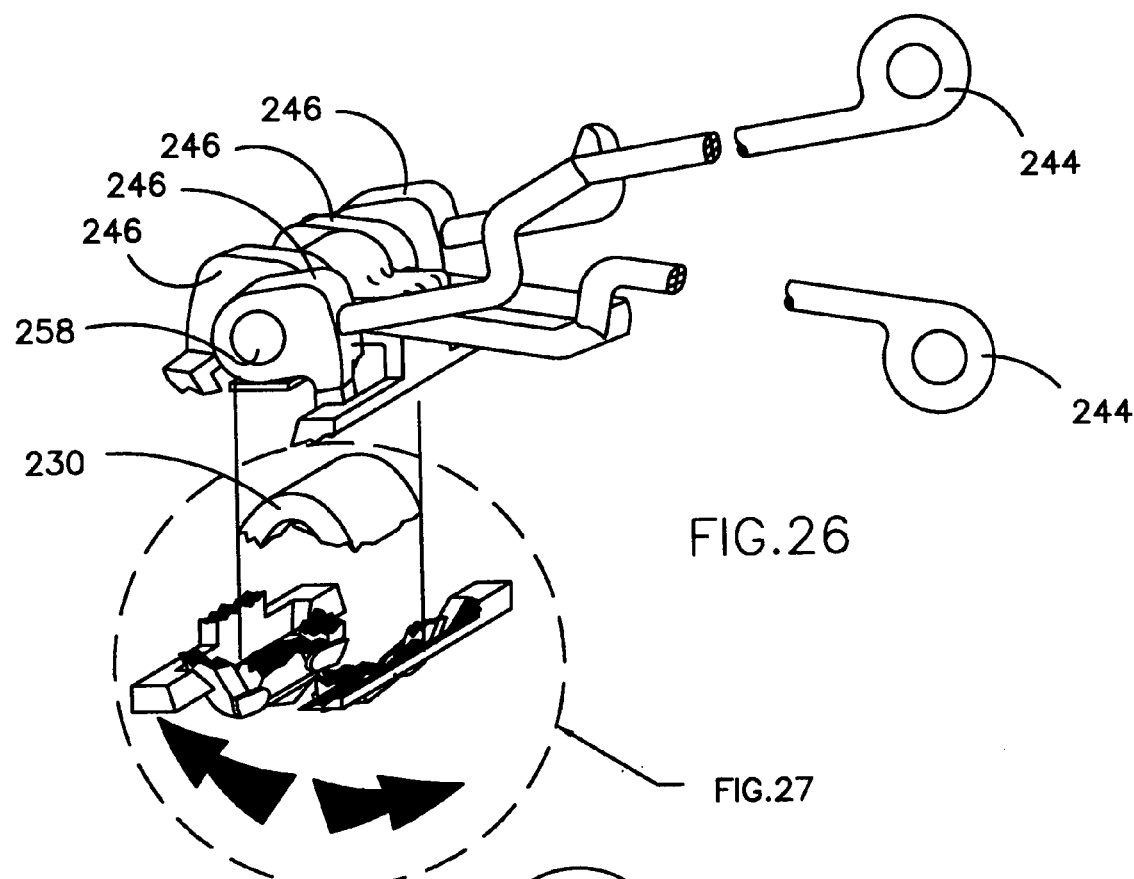
FIG. 26 is a perspective view of the staple insertion tool according to the present invention in the open staple releasing mode.
Figure 27:
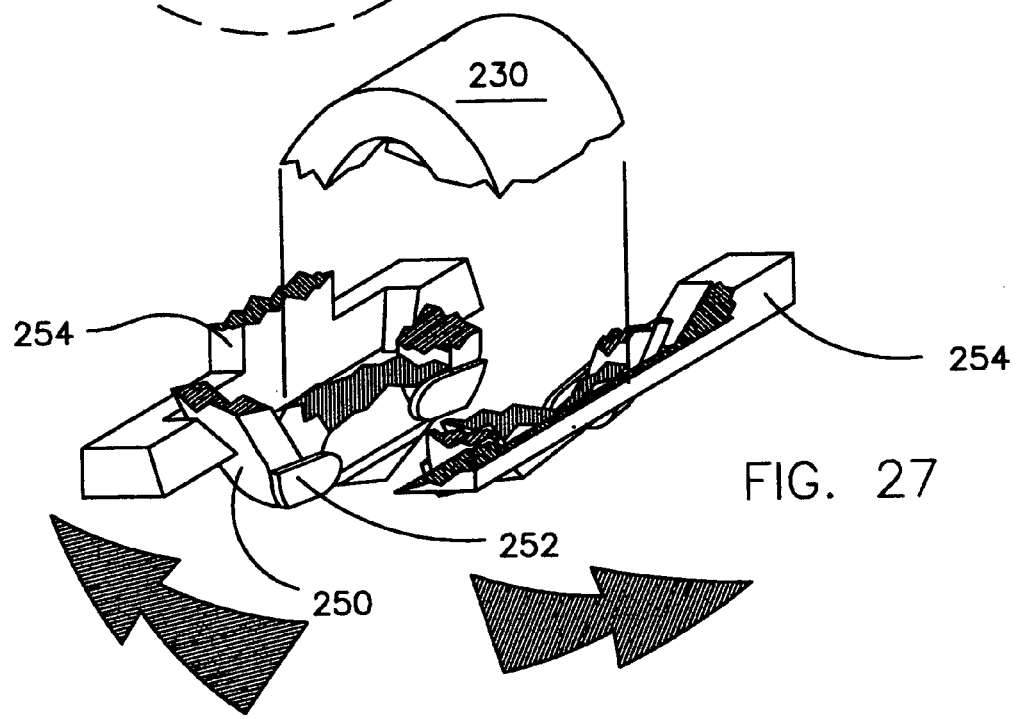
FIG. 27 is a detailed perspective view, partially broken away, of the gripping portion of the tool as illustrated in FIG. 26.

The staples 230 employed in the above-noted embodiment are inserted using an insertion instrument generally indicated at 240 as illustrated in FIGS. 18 through 27. It will be noted that prior to insertion, the staple must be transported by the surgeon within the eye. Thus, the instrument, which is described in detail hereinbelow, is designed with safety features such that it is difficult to accidentally release the staple and further, once released, the staple automatically contrats and grippingly attaches to the iris. With the foregoing in mind, the instrument comprises a pair of manipulating rods or handles 242 having respective finger loops 244 at one end which assist the surgeon in one-handed operation during insertion of the instrument tip into the eye. The opposite ends of the respective handles divide into a U shaped bracket, which supports a block 246. In the center of the block 246 is a hole defining an opening 248. A finger 250 depends downward and inward and terminates in a gripping tab 252. Also provided is a locking plate 254 which includes a U-shaped block having an elongate bore 256 therein which allows it to be placed in alignment with the other blocks 246 when pivot pin 258 is aligned therein. A rectangular plate 260 is attached to the underside of the block as best shown in FIG. 19. The plate 260 establishes the limit of vertical travel staple 230 in the instrument.

In operation, the instrument handles are spread apart to spread the fingers 250 and locking plates 254. The staple 230 is then inserted such that the arched mid-section abuts plate 260 and the legs are situated between opposing pairs of gripping tabs 252. The handles are then moved together which causes the staple to be caught between locking plate 254, gripping tabs 252 and plate 260. Continued pressure causes the staples opening to become expanded. The instrument is then inserted in the eye such that the staples overlies in straddling relation the haptic. The manipulating rods are then moved apart from each other which causes the locking plate 254 to move outward, which in turn permits the staple 230 to slide out from between the gripping fingers and to contract into the iris.

Figure 10:
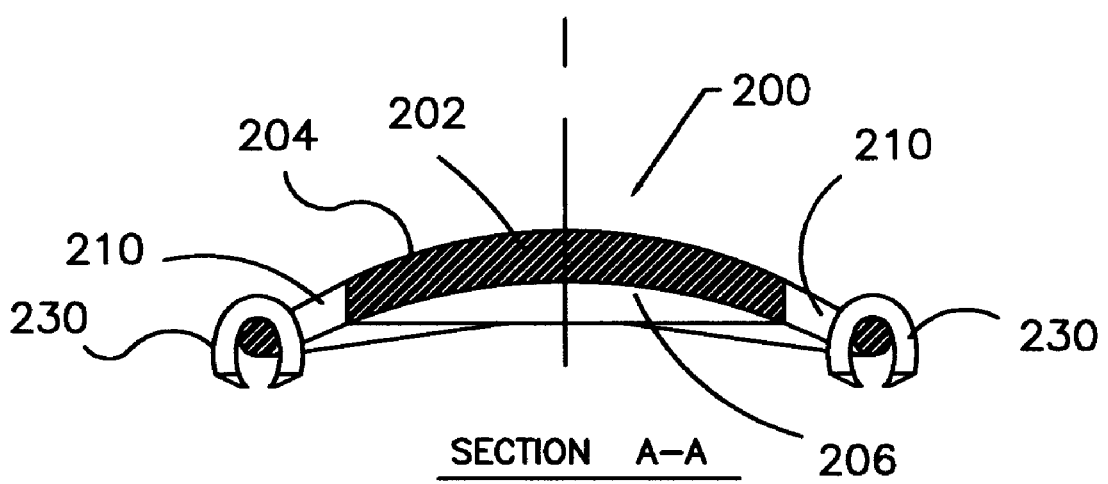
FIG. 10 is a sectional view taken along line A—A of the embodiment of the implant lens of FIG. 9.
Figure 10A:
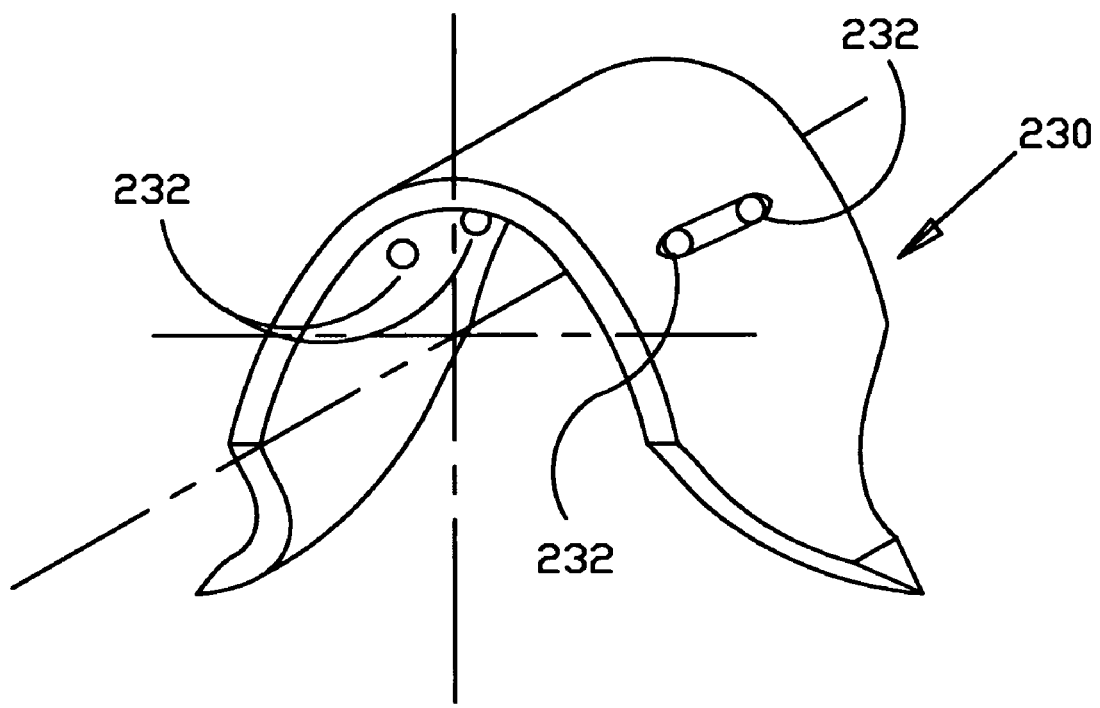
FIG. 10a is a perspective view of a staple used to attach the implant lens according to the present invention.
Figure 10B:
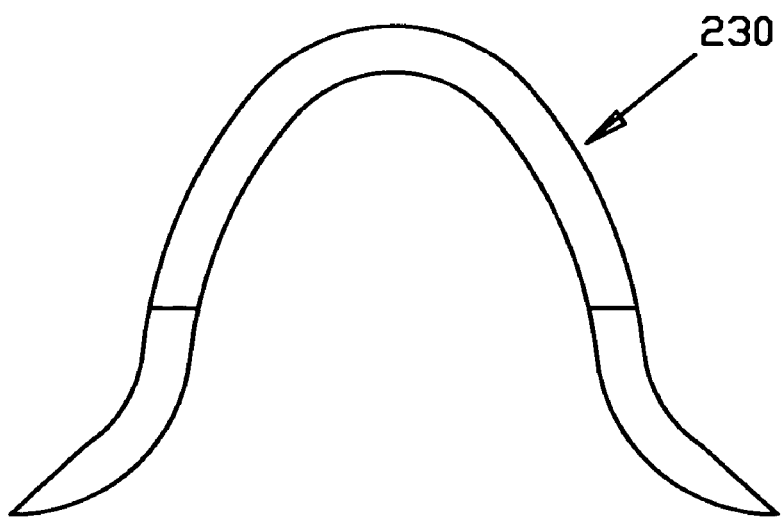
FIG. 10b is an end view of a staple used to attach the implant lens according to the present invention.

In another embodiment of the staple, as shown in FIGS. 10a and 10b, one or more fixation points or indentations 232 are provided on either side which correspond to fixation point adapters on an insertion tool, such as forceps. In operation, the staple would be placed between opposing tips of the forceps. If indentations are provided, they would be aligned such that the corresponding protrusions are inserted therein. During insertion within the eye and placement over the iris and the haptic, the staple is compressed by the forceps. When properly positioned on the surface of the eye, slight downward pressure is exerted and the forceps released, causing the staple to expand and become drawn into the iris. It will be noted that the tensioned and relaxed states of the staple, as shown in FIGS. 10a and 10b could be reversed with equal efficacy.

Figure 15:
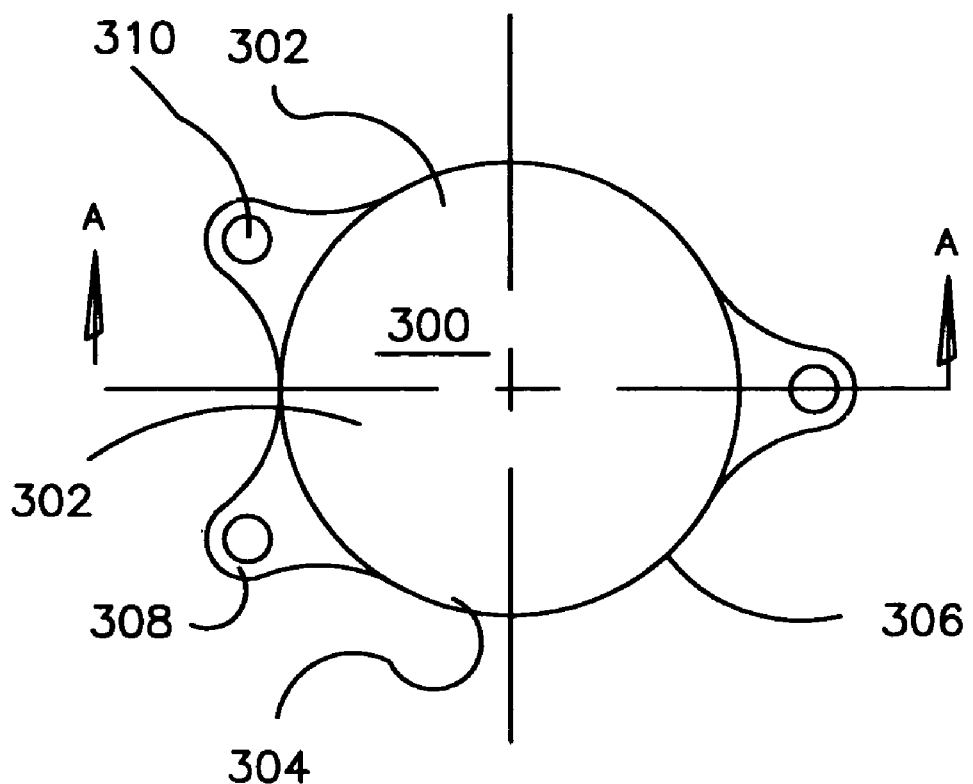
FIG. 15 is a plan view of a third embodiment of the implant lens according to the present invention.
Figure 16:
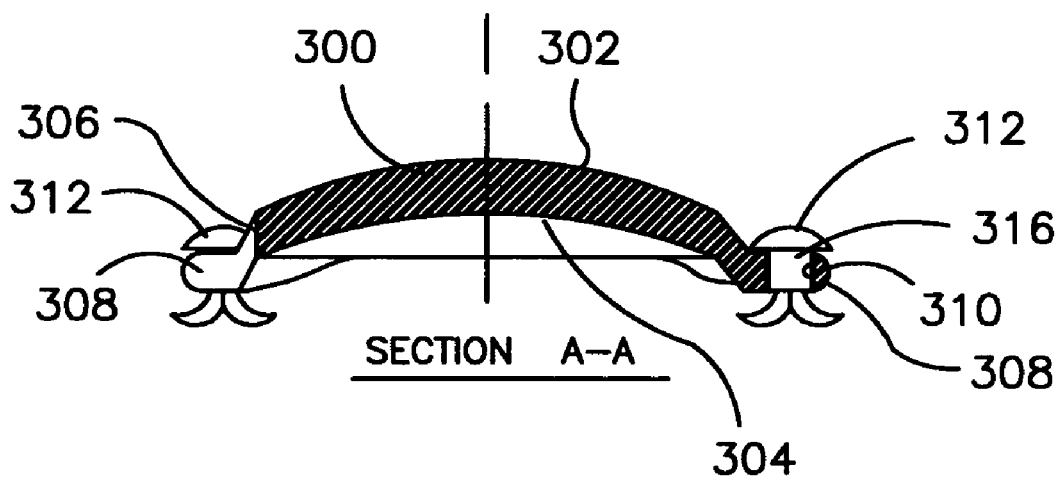
FIG. 16 is a sectional view taken along line A—A of FIG. 15 of the implant lens according to the present invention.
Figure 17:
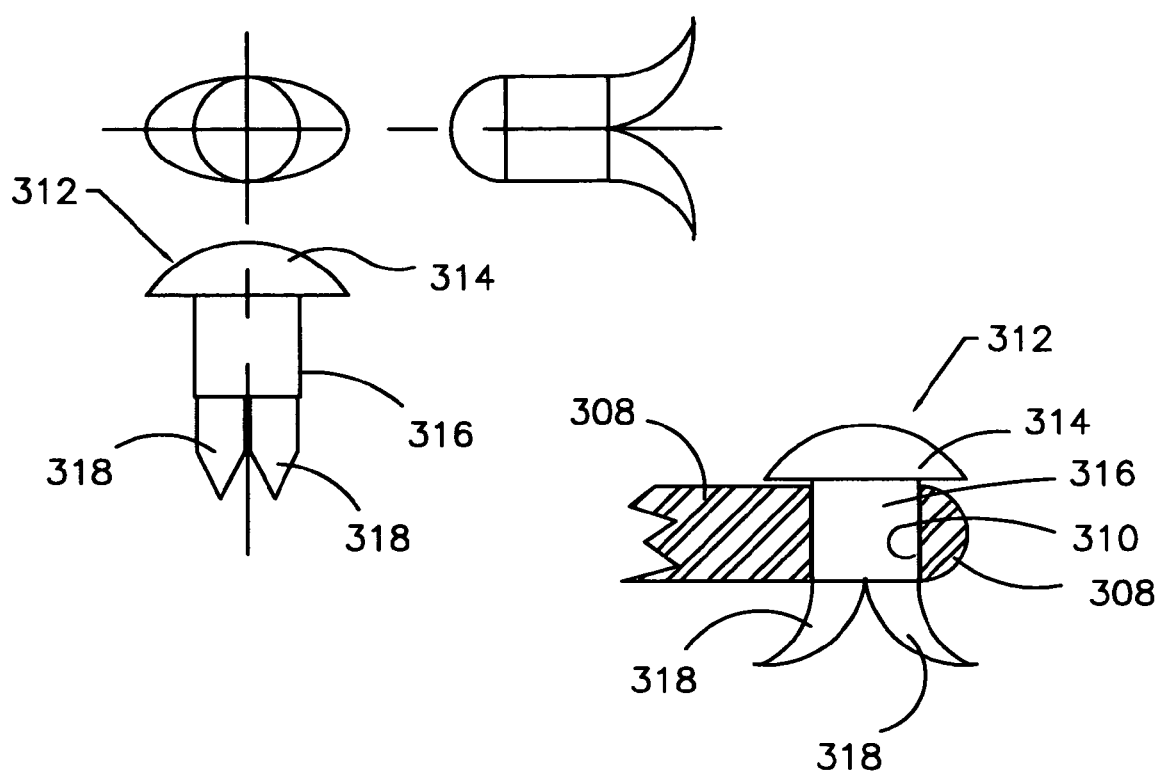
FIG. 17 is a side view of the fastening means according to the present invention being pushed downward through the haptic and into the iris.
Figure 18:
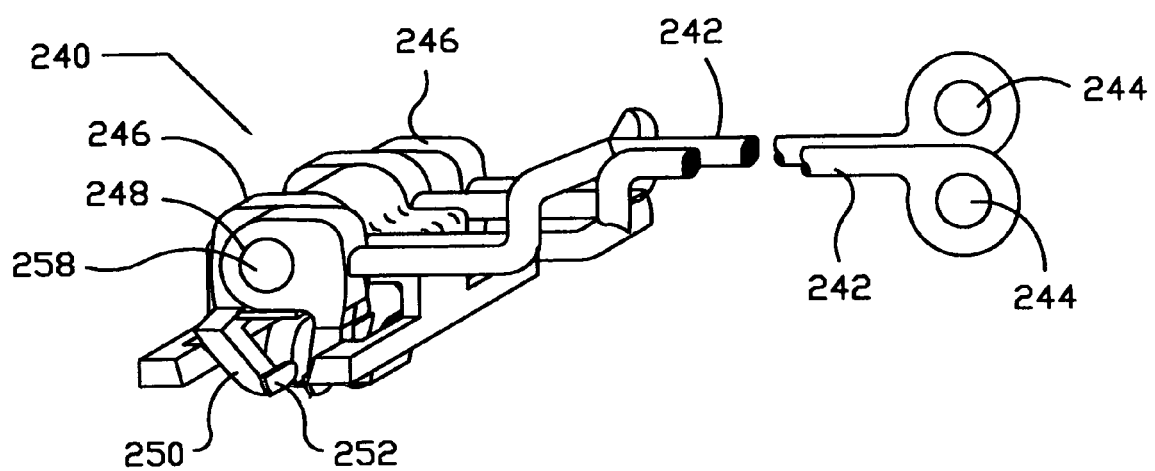
FIG. 18 is a perspective view of the staple insertion tool according to the present invention.

A third embodiment of the invention is illustrated in FIGS. 15 through 17. In that embodiment an optical means or implant 300 for producing a preselected optical effect on light entering the eye and adapted to be implanted in overlying relation to the iris 52 is employed. The implant 300 includes an anterior side 302 and a posterior side 304 and an outer peripheral edge 306. A single or plurality of haptic means or haptics 308 are connected to the implant 300 such that at least one includes a hole defining an opening 310. A fastening means 312 for fixing the position of the intraocular lens on the iris is provided.

The fastening means or fastener 312 is adapted to be inserted within the opening 310 and to expandingly grip the iris tissue. More specifically, the fastening means 312 comprises a shaft having a top end 314 and a bottom end 316. Located at the bottom end 316 is a flexible barb 318 and the top end 314 has a diameter that is greater than the diameter of opening 310. As illustrated in FIG. 17, the barbs are arranged to point outwardly when relaxed.

In operation, the implant 300 is centered over the iris. Then fastener 312 is gripped with forceps (not shown) such that the barbs 318 are compressed. The fastener 312 is then guided into the opening 310 and downward pressure is then gently exerted to push the staple 312 through opening 310. As the barbs exit the opening on the anterior side 304, they contact the iris tissue and begin to expand. When the top end 314 contacts the upper surface of the haptic 308, the barbs penetrate the iris (approximately one-half of the thickness of the iris in the illustrated embodiment) and the position of the implant 300 is fixed in the eye. The foregoing procedure is repeated for each haptic and the number of fasteners employed will depend on the geometry of the specific implant 300 chosen by the surgeon.

Figure 28:
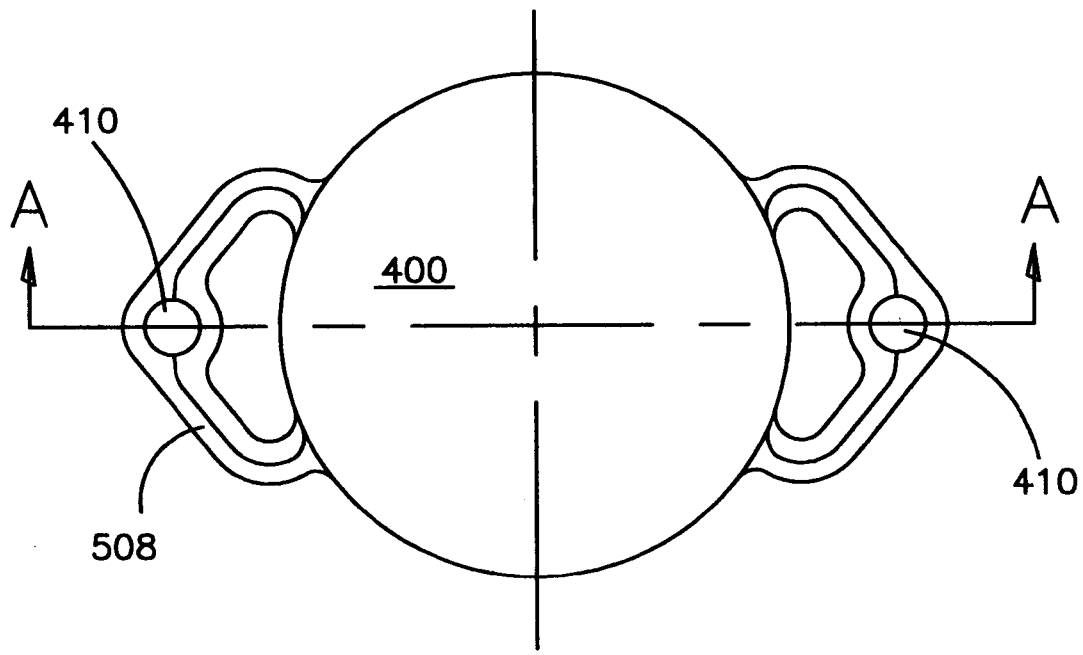
FIG. 28 is a plan view of a forth embodiment of the implant lens according to the present invention.
Figure 29:
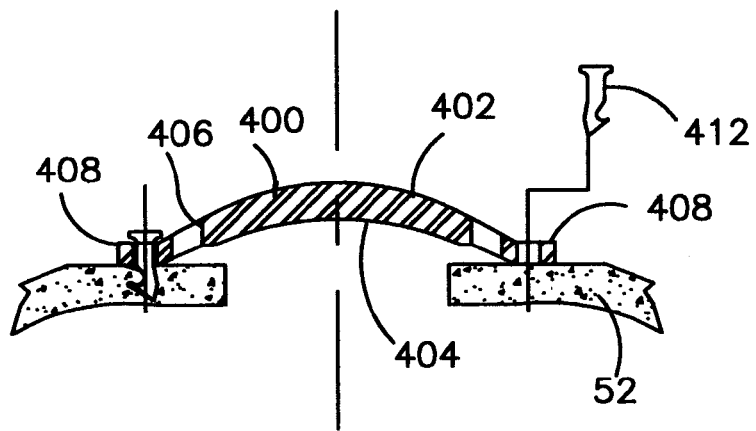
FIG. 29 is a sectional view taken along line A—A of FIG. 28 of the implant lens according to the present invention.
Figure 30:
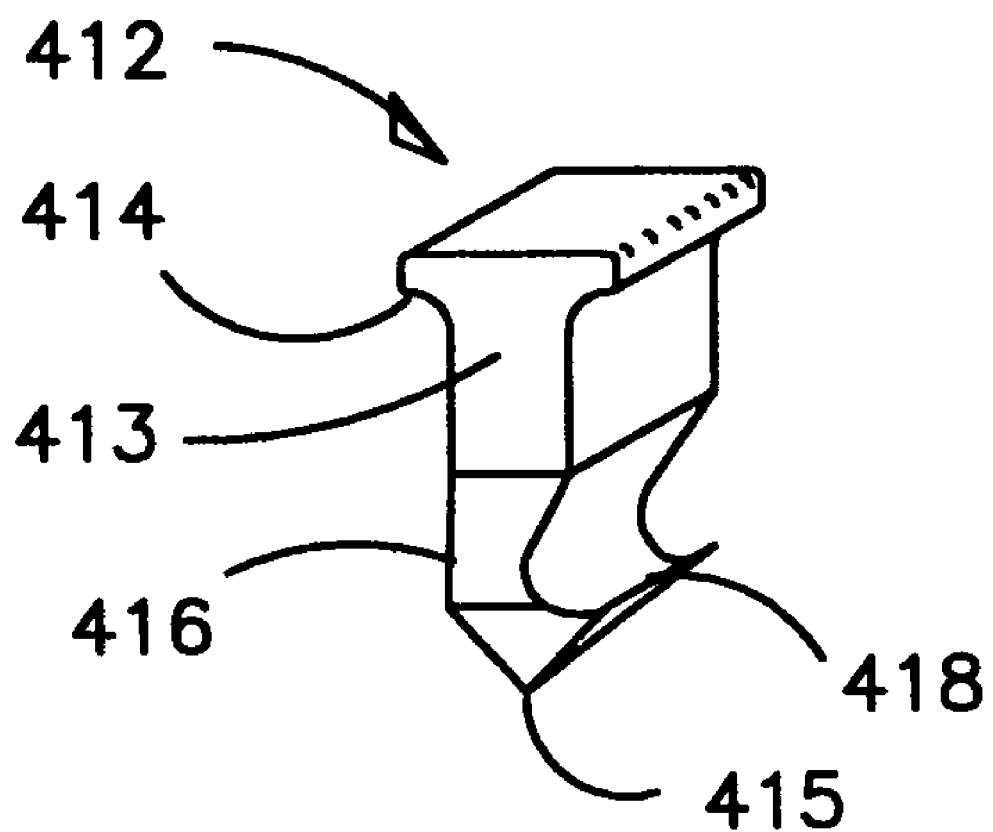
FIG. 30 is a perspective view of the forth embodiment of the fastening means according to the present invention.

A forth embodiment of the invention is illustrated in FIGS. 28 through 30. In that embodiment an optical means or implant 400 for producing a preselected optical effect on light entering the eye and adapted to be implanted in overlying relation to the iris 52 is employed. The implant 400 includes an anterior side 402, a posterior side 404 and an outer peripheral edge 406. A single or plurality of haptic means or haptics 408 are connected to the implant 400 such that at least on includes a hole defining an opening 410. A fastening means or fastener 412 for fixing the position of the intraocular lens on the iris is provided. The fastener 412 comprises a shaft 413 having a top end 414 and an iris fixation end or bottom end 416. The bottom end terminates in an edge 415. Located proximate the edge 415 is a cutout portion which forms a flexible hook or barb 418. The top end 414 has a diameter that is greater than the diameter of opening 410. It will be noted that the opening 410 in the haptic is circular and shaft 413 is rectangular. Also, while not illustrated, the fastener 412 may be molded to be integral with the haptic 408 and to extend downwardly therefrom. Alternatively, the fastener 412 may be fabricated as a separate unit and press fit within opening 410 so that it slides therein so that the entire intraocular lens/fastener can be inserted within the eye in a single motion.

Figure 31:
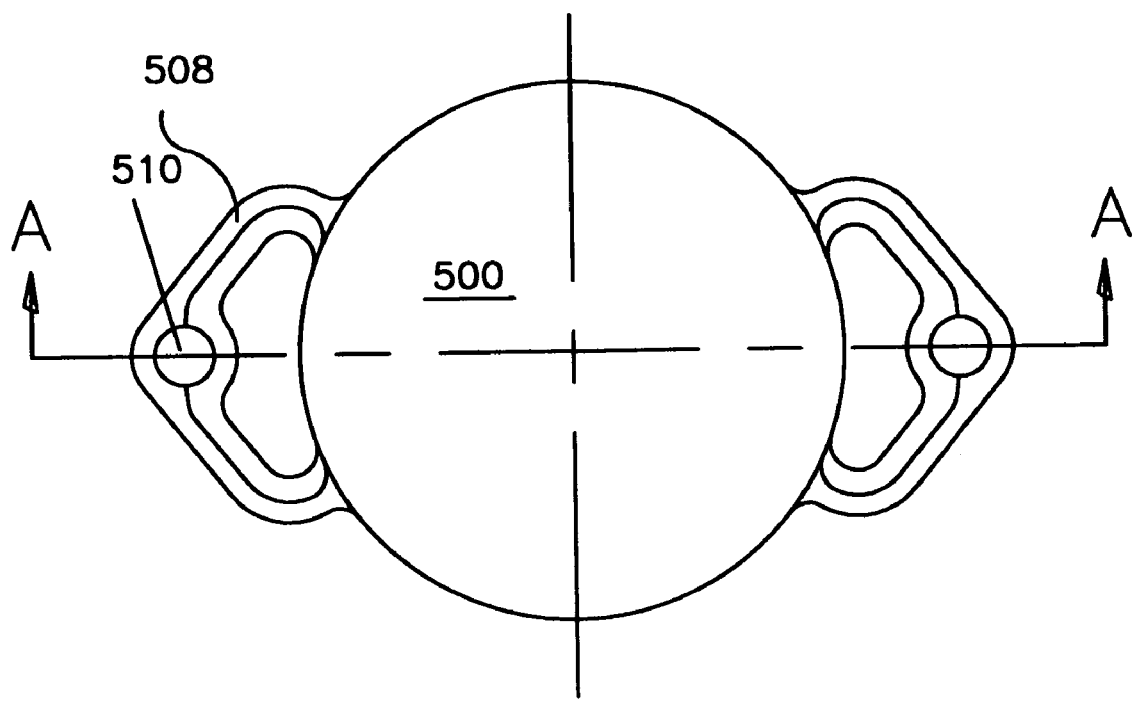
FIG. 31 is a plan view of a fifth embodiment of the implant lens according to the present invention.
Figure 32:
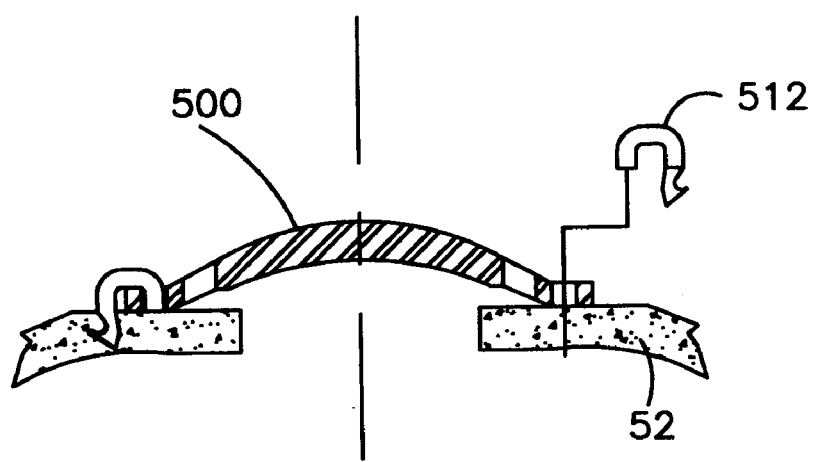
FIG. 32 is a sectional view taken along line A—A of FIG. 31 of the implant lens according to the present invention.
Figure 33:
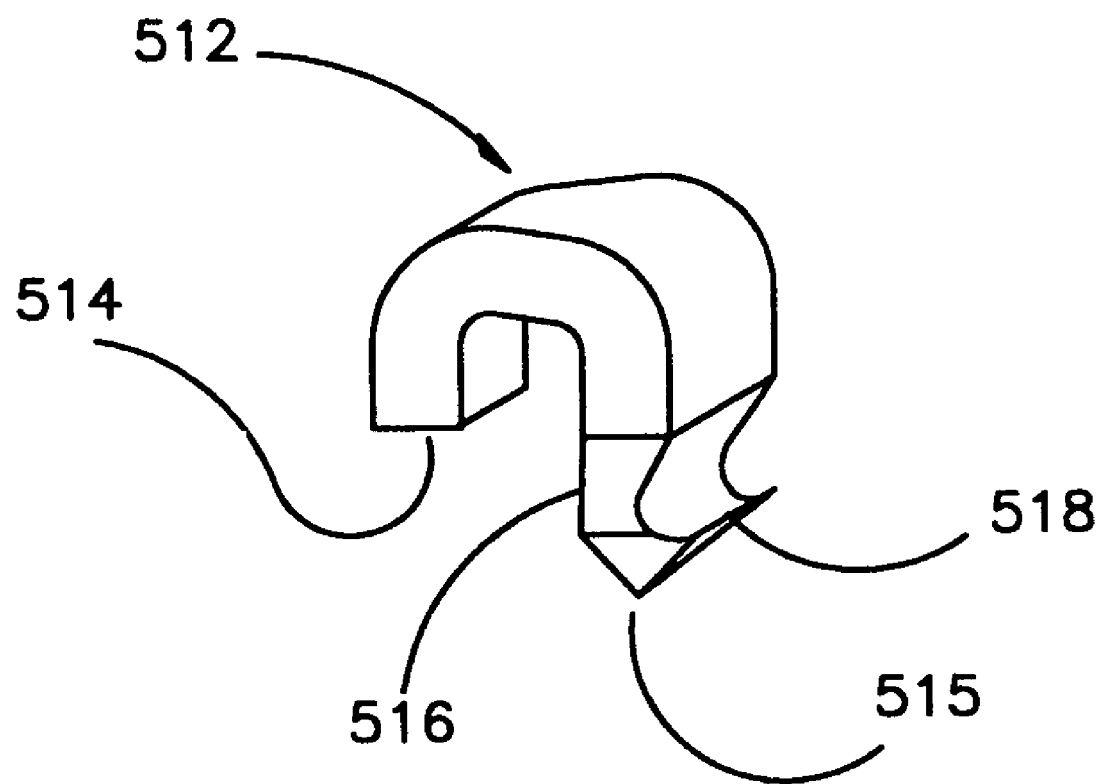
FIG. 33 is a perspective view of the fifth embodiment of the fastening means according to the present invention.

In operation, the implant 400 is centered over the iris. Then the fastener 412 is gripped with forceps (not shown) and is guided into opening 410 and downward pressure is then gently exerted to push the edge into the iris. Continued downward pressure engages the barb such that it becomes barbingly embedded within the iris thereby anchoring the intraocular lens on the iris. The foregoing procedure is repeated for each haptic and the number of fasteners employed will, of course, depend on the geometry of the specific implant chosen by the surgeon. In a related embodiment, shown in FIGS. 31 through 33, the fastener 512, rather than being linear, is U-shaped as best illustrated in FIG. 33. The fastener 512 has a top end 514 which is adapted to be inserted within opening 510 of the haptic 508 on intraocular lens 500. The bottom end terminates in an edge 515. Located proximate the edge 515 is a cutout portion which forms a flexible hook or barb 518. Attachment is substantially similar to the embodiment shown in FIGS. 28–30, but differing in that the fastener straddles the haptic.

Figure 34:
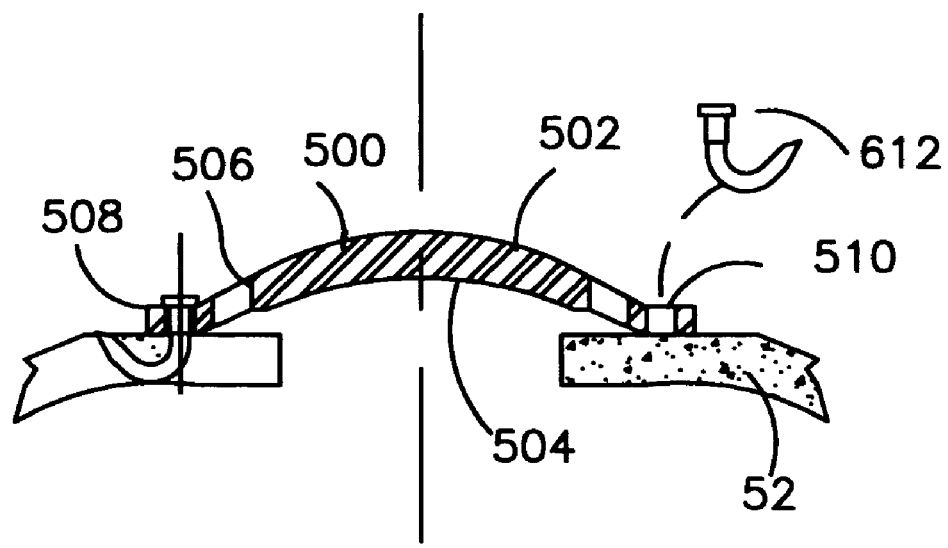
FIG. 34 a sectional view of the sixth embodiment of the fastening means according to the present invention.
Figure 35:
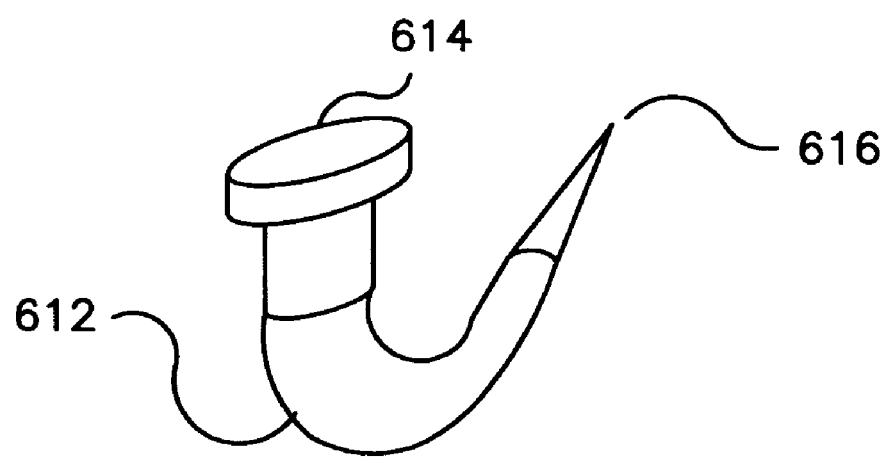
FIG. 35 is a perspective view of the sixth embodiment of the fastening means according to the present invention.
Figure 36A:
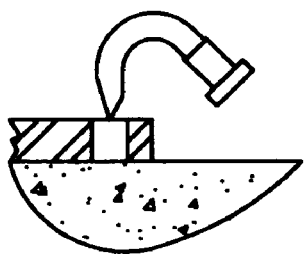
FIGS. 36(a) through 36(g) illustrate the sixth embodiment of the fastening means being employed to attach an intraocular lens to the anterior surface of the iris.
Figure 36B:
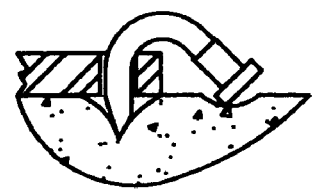
Figure 36C:
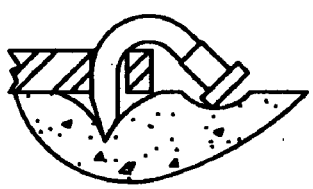
Figure 36D:
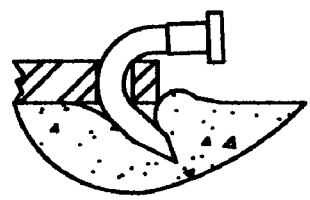
Figure 36E:
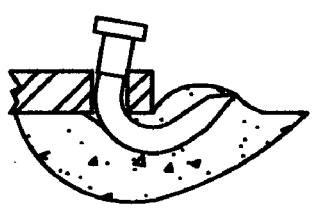
Figure 36F:
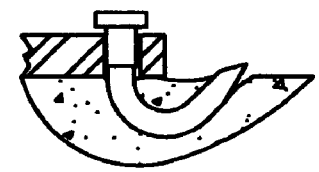
Figure 36G:
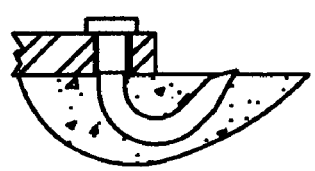

An alternate embodiment of the fastener is shown in FIGS. 34 through 36. In this embodiment, the fastening means or anchor 612 is an elongate bent shaft. The is anchor 612 has a securing head 614 at one end and a sharp point 616 adapted to pierce the iris tissue at the opposite end. The diameter of the securing head is greater than the diameter of the haptic opening and the remaining portion of the anchor is smaller than said opening to facilitate movement of the anchor therethrough. Further, as illustrated, the anchor is tapered with diameter decreasing as it nears point 616. In addition, the anchor 612 has a bend in its central portion, the center of the radius being situated to prevent unintentional rotating of the anchor out of the iris when pressure is placed on its lower extreme.

In use, the implant 500 is centered over the iris. The anchor 612 is gripped with forceps (not shown) an inverted such that the pointed tip 616 is guided into opening 510. After passing through opening 510, continued pressure causes the tip to depress the iris (FIGS. 36(a)–(c)), before penetrating the iris (FIG. 36(d)). Thereafter, with continued pressure the shaft arcingly moves further into the iris (FIGS. 36(e)–(g)) until the securing head rests on the surface of the haptic.

Figure 37A:
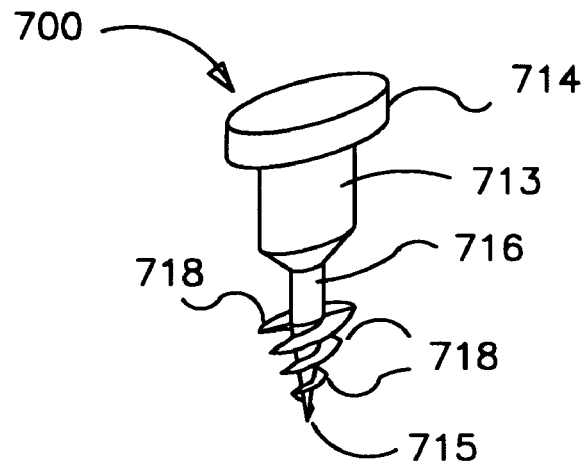
FIG. 37a is a perspective view of a seventh embodiment of a fastening means according to the present invention.
Figure 37B:
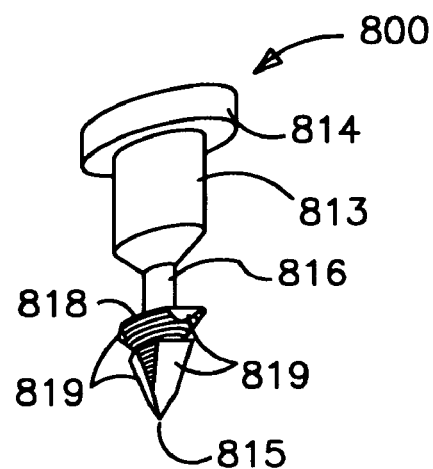
FIG. 37b is a perspective view of a variant of the seventh embodiment of the fastening means according to the present invention.

The fastening means may also take the form of an iris anchoring fastener device generally indicated at 700 and 800 in FIGS. 37a and 37b, respectively. The fastener 700 has a proximal end and a distal end, the proximal end has a securing head 714 of a diameter greater than the diameter of the haptic opening. A central shaft portion 713 of a diameter slightly smaller than the diameter of the haptic opening. The central shaft portion is tapered at its lower end and terminates in cylindrical section 716. Proximate the distal end is a threaded portion 718 which comprises an auger-type thread and which terminates in a point 715.

Figure 38:
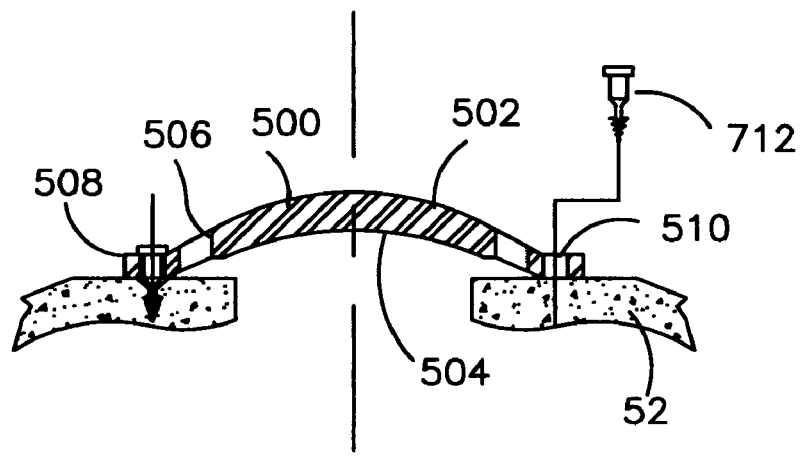
FIG. 38 is a sectional view of the seventh embodiment of the implant lens and fastening means according to the present invention.

In use, the fastening means 700 is inserted point 715 first into the haptic opening to the point where it contacts the surface of the iris as shown in FIG. 38. Thereafter, slight downward pressure is exerted to penetrate the iris surface and the fastener 712 is rotated and is drawn into the iris thus attaching the intraocular lens to the iris. A slightly different embodiment is shown in FIG. 37b. The fastener 800 has a proximal end and a distal end, the proximal end has a securing head 814 of a diameter greater than the diameter of the haptic opening. A central shaft portion 813 of a diameter slightly smaller than the diameter of the haptic opening. The central shaft portion is tapered at its lower end and terminates in cylindrical section 816. Proximate the distal end is a double trocar point 819. More specifically, the trocar point is widest at the distal end and has a flat head 818 which tapers to a point 815. Sides 819 are also tapered but are sharp and smooth while the opposite sides are taperingly terraced as the point is approached. In operation the fastener 800 is centered within the haptic opening. The surgeon would then push down on securing head 814 or pull down on shaft 813, as appropriate. This causes the tip 815 to pierce the surface of the iris. Pressure is then placed on the fastener until the securing head rests on or near the surface of the haptic. The trocar point acts as a barb to prevent the fastener from becoming accidentally dislodged from the iris.

Figure 39:
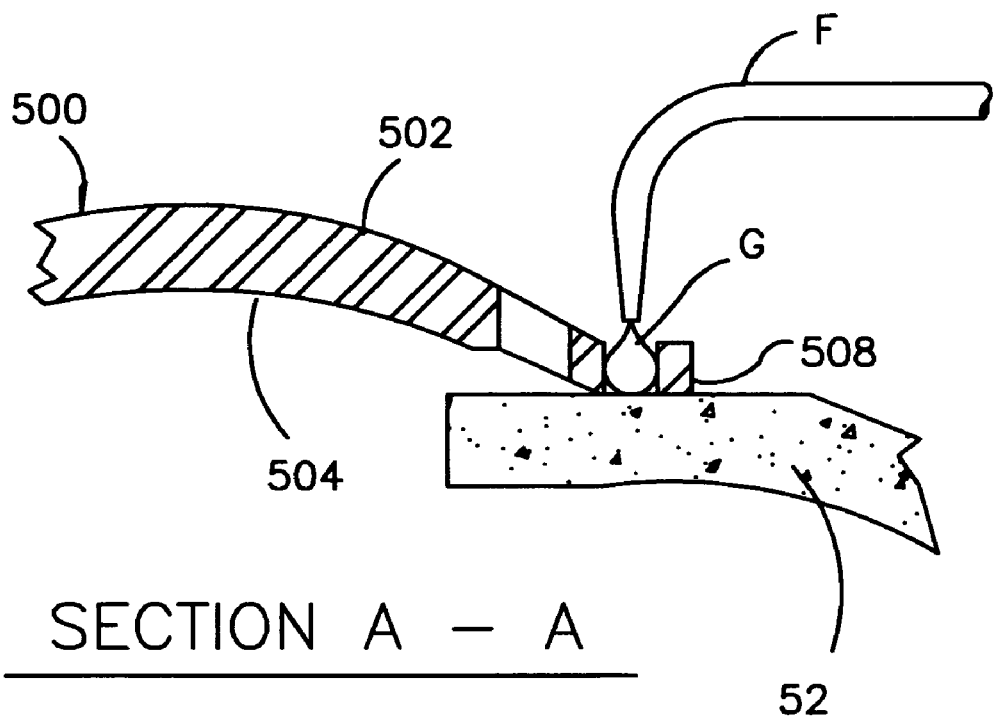
FIG. 39 is a sectional view of an intraocular lens being attached to the anterior surface of the iris via adhesive according to the present invention.
Figure 40:
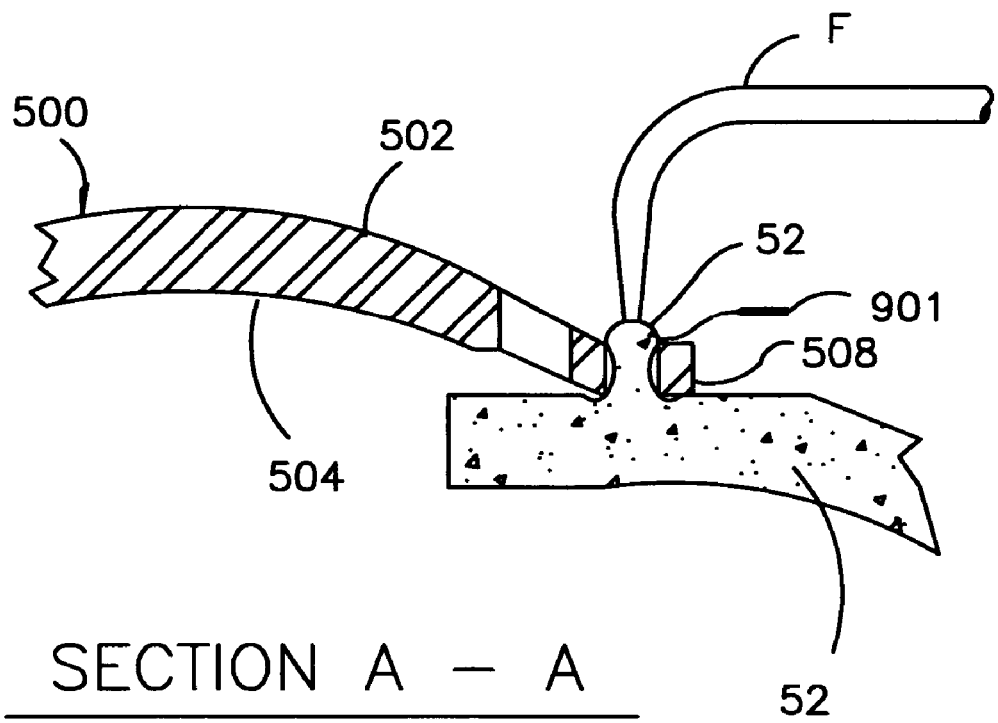
FIG. 40 is a sectional view of a portion of the iris being pinned employing a vacuum to pull the iris into the implant lens opening in the haptic and using a pin to attach the intraocular lens to the iris.

FIG. 39 illustrate another method of attaching the intraocular lens to the anterior surface of the iris. More specifically, once the intraocular lens is positioned as desired over the iris, forceps F is positioned over opening 510 in the haptic and a drop of adhesive or glue G is applied in the haptic opening to secure the intraocular lens 500 to the iris. FIG. 40 illustrates the intraocular lens being attached to the iris using vacuum forceps VF which pulls a portion of the iris tissue up into the opening. In the embodiment shown, a portion of the iris tissue extends above the anterior surface of the haptic and an iris attachment anchor or pin 901 is inserted therein which connects the intraocular lens to the iris. Thereafter, the iris tissue is released from the vacuum forceps.

The present invention, of course may be carried out in other specific ways than those herein set forth without departing from the spirit and essential characteristics of the invention. The present invention is therefore, to be considered in all respects as illustrative and not restrictive, and all changes coming within the meaning and range of the appended claims are intended to be embraced therein.

What is claimed is:

1. A method of fixating in the eye, an intraocular lens comprising the steps of:

inserting the intraocular lens having an optic for producing a preselected optical effect, the optic having an anterior side, a posterior side; and at least one haptic connected to the optic and extending outward from the optic and further, wherein the haptic includes an iris connector connecting the intraocular lens to the iris; and attaching the haptic to the iris between the sphincter muscle and the dilator muscle of the iris.

2. The method according to claim 1 further including a riser for maintaining the optic in a spaced relation from the surface of the iris.

3. The method according to claim 2 wherein the iris connector is constructed and arranged to penetrate less than the entire thickness of the iris.

4. The method according to claim 3 wherein the iris connector is constructed and arranged to penetrate the iris to a depth so as not to penetrate the pigment epithelium.

5. The method according to claim 1 wherein the optic is selected for the treatment of conditions selected from the group consisting of myopia, hyperopia, astigmatism and presbyopia.

6. A method of fixating in the eye, an intraocular lens comprising the steps of:

inserting the intraocular lens having an optic for producing a preselected optical effect, the optic having an anterior side, a posterior side and at least one haptic connected to the optic and extending outward from the optic and further, wherein a fastener is operatively associated with the haptic for connecting the intraocular lens to the iris;

and attaching the haptic is to the iris between the sphincter muscle and the dilator muscle of the iris.

7. The method according to claim 6 further including a riser for maintaining the optic in a spaced relation from the surface of the iris.

8. The method according to claim 6 wherein the fastener is constructed and arranged to penetrate less than the entire thickness of the iris.

9. The method according to claim 8 wherein the fastener is constructed and arranged to penetrate the iris to a depth so as not to penetrate the pigment epithelium.

10. The method according to claim 6 wherein the optic is selected for the treatment of conditions selected from the group consisting of myopia, hyperopia, astigmatism and presbyopia.

* * * * *